US007041872B2

(12) United States Patent
Lassner et al.

(10) Patent No.: US 7,041,872 B2
(45) Date of Patent: May 9, 2006

(54) ACYL COA:CHOLESTEROL ACYLTRANSFERASE RELATED NUCLEIC ACID SEQUENCES

(75) Inventors: Michael W. Lassner, Foster City, CA (US); Diane M. Ruezinsky, Woodland, CA (US)

(73) Assignee: Calgene LLC, Davis, CA (US)

( * ) Notice: Subject to any disclaimer, the term of this patent is extended or adjusted under 35 U.S.C. 154(b) by 506 days.

(21) Appl. No.: 10/157,855

(22) Filed: May 31, 2002

(65) Prior Publication Data

US 2002/0170091 A1    Nov. 14, 2002

Related U.S. Application Data

(63) Continuation of application No. 09/326,203, filed on Jun. 4, 1999, now Pat. No. 6,444,876.

(60) Provisional application No. 60/108,389, filed on Nov. 12, 1998, provisional application No. 60/088,143, filed on Jun. 5, 1998.

(51) Int. Cl.
*A01H 5/00*        (2006.01)
*C12N 15/82*      (2006.01)

(52) U.S. Cl. ........................ 800/281; 435/619; 435/468; 536/23.2

(58) Field of Classification Search ................ 800/281, 800/298; 435/419, 468, 619; 536/23.2
See application file for complete search history.

(56) References Cited

U.S. PATENT DOCUMENTS

| 5,298,421 A | 3/1994 | Davies et al. |
| 5,667,997 A | 9/1997 | Voelker et al. |
| 5,968,791 A | 10/1999 | Davies et al. |

FOREIGN PATENT DOCUMENTS

| WO | 94/09126 | 4/1994 |
| WO | 95/27791 | 10/1995 |
| WO | 97/45439 | 12/1997 |
| WO | 98/55631 | 12/1998 |

OTHER PUBLICATIONS

DeLuca, V. AgBiotech News and Information 5(6): 225N-229N, 1993.*
Bork, "Go hunting in sequence databases but watch out for the traps", *TIG*, vol. 12, No. 10, pp. 425-427 (1996).
Brenner, "Errors in genome annotation", *TIG*, vol. 15, No. 4, pp. 132-133 (1999).
Broun et al., "Catalytic Plasticity of Fatty Acid Modification Enzymes Underlying Chemical Diversity of Plant Lipids", *Science*, vol. 282, pp. 1315-1317 (1998).
Cases et al., "Identification of a gene encoding an acyl CoA:diacylglycerol acyltransferase, a key enzyme in triacylglycerol synthesis", *Proc. Natl. Acad. Sci. USA*, vol. 95, pp. 13018-13023 (1998).
Cases et al., "Cloning and Expression of a Candidate Gene for Diacylglycerol Acyltransferase", *FASEB Journal*, vol. 12, No. 5, p. A814 (1998).
Doerks, "Protein annotation: detective work for function prediction", *TIG*, vol. 14, No. 6, pp. 248-250 (1998).
Frentzen, "Acyltransferases from basic science to modified seed oils", *FETT-LIPID*, vol. 100, No. 4-5, pp. 161-166 (1998).
Hobbs et al., "Cloning of a cDNA encoding diacylglycerol acyltransferase from *Arabidopsis thaliana* and its functional expression", *FEBS Letters*, vol. 452, No. 3, pp. 145-149 (1999).
Marra et al., "AC W10786", EMBL Database (1996).
Marra et al., "AC AA457966", EMBL Database (1998).
Oelkers et al., "Characterization of Two Human Genes Encoding Acyl Coenzyme A:Cholesterol Acyltransferase-related Enzymes", *The Journal of Biological Chemistry*, vol. 273, No. 41, pp. 26765-26771 (1998).
Smith et al., "The challenges of genome sequence annotation or 'The devil is in the details'", *Nature Biotechnology*, vol. 15, pp. 1222-1223 (1997).
Töpfer et al., "Modification of Plant Lipid Synthesis", *Science*, vol. 268, pp. 681-686 (1995).
Van de Loo et al., "An oleate 12-hydroxylase from *Ricinus communis* L. is a fatty acyl desaturase homolog", *Proc. Natl. Acad. Sci. USA*, vol. 92, pp. 6743-6747 (1995).
Venter et al., "The Sequence of the Human Genome", *Science*, vol. 291, pp. 1304-1351 (2001).
Wilson et al., "AC 045245", EMBL Database (1998).
Woese et al., "Conservation of primary structure in 16S ribosomal RNA", *Nature*, vol. 254, No. 5495, pp. 83-86 (1975).
Yang et al., "Functional Expression of a cDNA to Human Acyl-coenzyme A:Cholesterol Acyltransferase in Yeast", *The Journal of Biological Chemistry*, vol. 272, No. 7, pp. 3980-3985 (1997).
Yu et al., "Molecular Cloning and Characterization of Two Isoforms of *Saccharomyces cerevisiae* Acyl-CoA:Sterol Acyltransferase", *The Journal of Biological Chemistry*, vol. 271, No. 39, pp. 24157-24163 (1996).
Zhou et al., "Modification of Seed Oil Content and Acyl (Continued)

Primary Examiner—Elizabeth F. McElwain
(74) Attorney, Agent, or Firm—Arnold & Porter LLP; Michael J. Roth

(57) ABSTRACT

By this invention, novel nucleic acid sequences encoding for acyl-CoA: cholesterol acyltransferase (ACAT) related proteins are provided, wherein said ACAT-like protein is active in the formation of a sterol ester and/or triacylylgycerol from a fatty acyl-CoA and sterol and/or diacylglycerol substrates. Also considered are amino acid and nucleic acid sequences obtainable from ACAT-like nucleic acid sequences and the use of such sequences to provide transgenic host cells capable of producing sterol esters and/or triacylglycerols.

14 Claims, 17 Drawing Sheets

OTHER PUBLICATIONS

Composition in the Brassicaceae by Expression of a Yeast sn-2 Acyltransferase Gene", *The Plant Cell*, vol. 9, pp. 909-923 (1997).

Baldo et al., "Signal Transduction Pathway of Acylation Stimulating Protein: Involvement of Protein Kinase C", *Journal of Lipid Research*, 36:1415-1426 (1995).

Bocan et al., "Comparison of CI-976, an ACAT Inhibitor, and Selected Lipid-Lowering Agents for Antiatherosclerotic Activity in Iliac-Femoral and Thoracic Aortic Lesions: A Biochemical, Morphological, and Morphometric Evaluation", *Arteriosclerosis and Thrombosis*, 11(6):1830-1843 (1991).

Brown et al., "Lipoprotein Metabolism in the Macrophage: Implications for Cholesterol Deposition in Atherosclerosis", *Ann. Review Biochem.*, 52:223-261 (1983).

Cadigan et al., "A Simple Method for Reconstitution of CHO Cell and Human Fibroblast Acyl Coenzyme A: Cholesterol Acyltransferase Activity into Liposomes", *Journal of Lipid Research*, 29:1683-1692 (1988).

Chang et al., "Molecular Cloning and Functional Expression of Human Acyl-Coenzyme A:Cholesterol Acyltransferase cDNA in Mutant Chinese Hamster Ovary Cells", *The Journal of Biological Chemistry*, 268(28):20747-20755 (1993).

Chang et al., "Acyl-Coenzyme A:Cholesterol Acyltransferase", *Ann. Rev. Biochem.*, 66:613-638 (1997).

da Costa et al., "Accumulation of 1,2-sn-Diradylglycerol with Increased Membrane-Associated Protein Kinase C May Be the Mechanism for Spontaneous Hepatocarcinogenesis in Choline-Deficient Rats", *The Journal of Biological Chemistry*, 268(3):2100-2105 (1993).

Fowler et al., "Characterization of Lipid-Laden Aortic Cells from Cholesterol-Fed Rabbits", *Laboratory Investigation*, 41(4):372-378 (1979).

Goldkorn et al., "The Rise and Fall of Ceramide and 1,2-Diacylglycerol (DAG): Modulation by Transforming Growth Factor-β1 (TGFβ1) and by Epidermal Growth Factor (EGF)", *Eicosanoids and Other Bioactive Lipids in Cancer, Inflammation, and Radiation Injury 2*, Chap. 62, pp. 461-472 (1997).

Scott M. Grundy, "Hypertriglyceridemia, Atherogenic, Dyslipidemia, and the Metabolic Syndrome", *The American Journal of Cardiology*, 81(4A):18B-25B (1998).

Jamdar et al., "Triacylglycerol Biosynthetic Enzymes in Lean and Obese Zucker Rats", *Biochimica et Biophysica Acta*, 1255:237-243 ((1995).

Koya et al., "Protein Kinase C Activation and the Development of Diabetic Complications", *Diabetes*, 47:859-866 (1998).

Kugiyama et al., "Association of Remnant Lipoprotein Levels with Impairment of Endothelium-Dependent Vasomotor Function in Human Coronary Arteries", *Circulation*, 97:2519-2526 (1998).

Lupu et al., "Development of Intracellular Lipid Deposits in the Lipid-Laden Cells of Atherosclerotic Lesions: A Cytochemical and Ultrastructural Study", *Atherosclerosis*, 67:127-142 (1987).

Okumura et al., "Decreased 1,2-Diacylglycerol Levels in Myopathic Hamster Hearts During the Development of Heart Failure", *J. Mol. Cell Cardiol.*, 23:409-416 (1991).

Owen et al., "Overt and Latent Activities of Diacylglycerol Acytransferase in Rat Liver Microsomes: Possible Roles in Very-Low Density Lipoprotein Triacylglycerol Secretion", *Biochem. J.*, 323:17-21 (1997).

Pai et al., "Overexpression of Protein Kinase C β1 Enhances Phospholipase D Activity and Diacylglycerol Formation in Phorbol Ester-Stimulated Rat Fibroblasts", *Proc. Natl. Acad. Sci. USA*, 88:598-602 (1991).

Ross et al., "Selective Inhibition of Acyl Coenzyme A: Cholesterol Acyltransferase by Compound 58-035", *The Journal of Biological Chemistry*, 259(2):815-819 (1984).

Schaffner et al., "Arterial Foam Cells With Distinctive Immunomorphologic and Histochemical Features of Macrophages", *American Journal of Pathology*, 100(1):57-80 (1980).

Tabas et al., "Inhibition of Acyl Coenzyme A:Cholesterol Acyl Transferase in J774 Macrophages Enhances Down-Regulation of the Low Density Lipoprotein Receptor and 3-Hydroxy-3-Methylglutaryl-Coenzyme A Reductase and Prevents Low Density Lipoprotein-Induced Cholesterol Accumulation", *The Journal of Biological Chemistry*, 261(7): 3147-3155 (1986).

Uelmen et al., "Tissue-Specific Expression and Cholesterol Regulation of Acylcoenzeme A:Cholesterol Acyltransferase (ACAT) in Mice", *The Journal of Biological Chemistry*, 270(44):26192-26201 (1995).

Yang et al., "Structural Basis of Ligand Discrimination by Two Related RNA Aptamers Resolved by NMR Spectroscopy", *Science*, 272:1343-1356 (1996).

Yu et al., "Molecular Cloning and Characterization of Two Isoforms of *Saccharomyces cerevisiae* Acyl-CoA:Sterol Acyltransferase", *The Journal of Biological Chemistry*, 271 (39):24157-24163 (1996).

* cited by examiner

```
CTCTCGTGAATCCTTTTTCCTTTCTTCTTCTTCTTCTCTTCAGAGAAAACTTTGCTTCTCTTT
CTATAAGGAACCAGACACGAATCCCATTCCCACCGATTTCTTAGCTTCTTCCTTCAATCCGC
TCTTTCCCTCTCCATTAGATTCTGTTTCCTCTTTCAATTTCTTCTGCATGCTTCTCGATTCTC
TCTGACGCCTCTTTTCTCCCGACGCTGTTTCGTCAAACGCTTTTCGAAATGGCGATTTTGG
ATTCTGCTGGCGTTACTACGGTGACGGAGAACGGTGGCGGAGAGTTCGTCGATCTTGATA
GGCTTCGTCGACGGAAATCGAGATCGGATTCTTCTAACGGACTTCTTCTCTCTGGTTCCGA
TAATAATTCTCCTTCGGATGATGTTGGAGCTCCCGCCGACGTTAGGGATCGGATTGATTCC
GTTGTTAACGATGACGCTCAGGGAACAGCCAATTTGGCCGGAGATAATAACGGTGGTGGC
GATAATAACGGTGGTGGAAGAGGCGGCGGAGAAGGAAGAGGAAACGCCGATGCTACGTTT
ACGTATCGACCGTCGGTTCCAGCTCATCGGAGGGCGAGAGAGAGTCCACTTAGCTCCGAC
GCAATCTTCAAACAGAGCCATGCCGGATTATTCAACCTCTGTGTAGTAGTTCTTATTGCTGT
AAACAGTAGACTCATCATCGAAAATCTTATGAAGTATGGTTGGTTGATCAGAACGGATTTC
TGGTTTAGTTCAAGATCGCTGCGAGATTGGCCGCTTTTCATGTGTTGTATATCCCTTTCGA
TCTTTCCTTTGGCTGCCTTTACGGTTGAGAAATTGGTACTTCAGAAATACATATCAGAACCT
GTTGTCATCTTTCTTCATATTATTATCACCATGACAGAGGTTTTGTATCCAGTTTACGTCAC
CCTAAGGTGTGATTCTGCTTTTTTATCAGGTGTCACTTTGATGCTCCTCACTTGCATTGTGT
GGCTAAAGTTGGTTTCTTATGCTCATACTAGCTATGACATAAGATCCCTAGCCAATGCAGC
TGATAAGGCCAATCCTGAAGTCTCCTACTACGTTAGCTTGAAGAGCTTGGCATATTTCATG
GTCGCTCCCACATTGTGTTATCAGCCAAGTTATCCACGTTCTGCATGTATACGGAAGGGTT
GGGTGGCTCGTCAATTTGCAAAACTGGTCATATTCACCGGATTCATGGGATTTATAATAGA
ACAATATATAAATCCTATTGTCAGGAACTCAAAGCATCCTTTGAAAGGCGATCTTCTATATG
CTATTGAAAGAGTGTTGAAGCTTTCAGTTCCAAATTTATATGTGTGGCTCTGCATGTTCTA
CTGCTTCTTCCACCTTTGGTTAAACATATTGGCAGAGCTTCTCTGCTTCGGGGATCGTGAA
TTCTACAAAGATTGGTGGAATGCAAAAAGTGTGGGAGATTACTGGAGAATGTGGAATATGC
CTGTTCATAAATGGATGGTTCGACATATATACTTCCCGTGCTTGCGCAGCAAGATACCAAA
GACACTCGCCATTATCATTGCTTTCCTAGTCTCTGCAGTCTTTCATGAGCTATGCATCGCAG
TTCCTTGTCGTCTCTTCAAGCTATGGGCTTTTCTTGGGATTATGTTTCAGGTGCCTTTGGT
CTTCATCACAAACTATCTACAGGAAAGGTTTGGCTCAACGGTGGGGAACATGATCTTCTGG
TTCATCTTCTGCATTTTCGGACAACCGATGTGTGTGCTTCTTTATTACCACGACCTGATGAA
CCGAAAAGGATCGATGTCATGAAACAACTGTTCAAAAAATGACTTTCTTCAAACATCTATGG
CCTCGTTGGATCTCCGTTGATGTTGTGGTGGTTCTGATGCTAAAACGACAAATAGTGTTAT
AACCATTGAAGAAGAAAAGACAATTAGAGTTGTTGTATCGCA
```

>protein
MAILDSAGVTTVTENGGGEFVDLDRLRRRKSRSDSSNGLLLSGSDNNSPSDDVGAPADVRDR
IDSVVNDDAQGTANLAGDNNGGGDNNGGGRGGGEGRGNADATFTYRPSVPAHRRARESPL
SSDAIFKQSHAGLFNLCVVVLIAVNSRLIIENLMKYGWLIRTDFWFSSRSLRDWPLFMCCISLS
IFPLAAFTVEKLVLQKYISEPVVIFLHIIITMTEVLYPVYVTLRCDSAFLSGVTLMLLTCIVWLKLV
SYAHTSYDIRSLANAADKANPEVSYYVSLKSLAYFMVAPTLCYQPSYPRSACIRKGWVARQFA
KLVIFTGFMGFIIEQYINPIVRNSKHPLKGDLLYAIERVLKLSVPNLYVWLCMFYCFFHLWLNIL
AELLCFGDREFYKDWWNAKSVGDYWRMWNMPVHKWMVRHIYFPCLRSKIPKTLAIIIAFLVS
AVFHELCIAVPCRLFKLWAFLGIMFQVPLVFITNYLQERFGSTVGNMIFWFIFCIFGQPMCVLL
YYHDLMNRKGSMS

Figure 1

GTAAGCTTCAAGAGCTTAGCATANTTCCTGGTTGCCCCTANCATTATGTTACCAGCCAANCTATCCTGCACACCTTATA
TTCGAAAGGGTTGGCTGTTTCGCCAACTGTTCAACTTGTCAACTTGTCAACTTGTCAACAGGAGTTATGGATTTATAATAGAACAATACA
TAATCCCATTGTACAAATTCACAGCATCCTCAAGGGAAACCTTCTTTACGCCATCGAGAGAGTTCTGAAG

CTGCTTTGTATCTGGTGTGTCACGTTGATGCTATTAACTTGCATTGTGTGGTTAAAATTGGTGTCATATGCACATACAAAC
TATGATATGAGAGCACTTACTGTTTCGAATGAAAAGGGAGAAACATTACCAATACTTGATATGGAGTATCCGTACACT
GTGACCTTCAGGAGTTGGCATACTTCATGGTTGCTCCTACATTATGCTATCAGACAAGCTATCCTCGCACACCTTCAGT
TCGAAAGGGTTGGGTGTTTCGTCAACT

GTGGAATGCCAAAACTGTGAAGATTATTGGAGGATGTGGAATATGCCTGTTCACAAATGGATCCGCCACCTATATT
TTCCATGTTTAAGGCACGGTATACCAAAGGCCGTTGCTCTTTAATTGCCTTCCTGGTTCTGTCTTATTCCATGAGCTGT
GCATCGCTGTTCCTTGCCCACATATTCAAGTNGTGGGTTTCNGNGGAATTNAGTTCAGGTNCCTTGGGTTTCNACCNNA
ATTNNTNGGCNAAAAATTCCNNGAACCCCGGGGG

AACGGAATTGAGACTCCAGAGAATATGCCAAAATGTATTAATAATTGTCACAACTTGGAAGGCTTTTGGAAAAACTGGCA
TGCTTCCTTCAACAAGTGCTTGTGAGGTATATACATTCCCTGGGGATCTAAGAAAAGCTACTAAATGTGTGGG
TTGTTTCACATTGTTGCAATCTTGCATGGAAGCTTCTTTCATGGGAAGCTTCTTCATGGGCATGGTTGACGTGTTATTCTTC
ATCCCTGAGTTGGTTTT

Figure 2

AGAAAATGAACATGCCTGTGCATAAATGGATTGTTCGTCATATATTTCCTTGCATGGGAAATGGTATATCAAAGGA
AGTTGCTGTTTTATATCGTTCTGTTCTTGCTGTACTTCATGAGTTATGTGTTCCCTGCCACATACTCAAGTT
CTGGGCTTTTTTAGGAATCATGCTTCAGATTCCCCTCATCATATTGACATCATATTGACACTGACACA
ATGGTTGGCAATA

TGAAGTATGGCTTATTAATAAGATCTGGCTTTGGTTAATGCTACATCATTGGGAGACTGGCCACTGCTAATGTGTTGC
CTTAGTCTACCCATATTCCCCTGGTGCATTTGCAGTCGAAAAGTTGGCATTCAACAATCTCATTAGTGATCCTGCTAC
TACCTGTTTCACATCCTTTTACAACATTTGAAATTGTATATCCAGTGCTCGTGATTCTTAAGTGTGATTCTGCAGTTT
TATCAGGCTTTGTG

GAAGTATGGCTTATTAATAAGATCTGGCTTTGGTTAATGCTACATCATTGGGAGACTGGCCACTGCTAATGTGTTGCC
TTAGTCTACCCATATTCCCCTGGTGCATTTGCAGTCGAAAAGTTGGCATTCAACAATCTCATTAGTGATCCTGCTACT
ACCTGTTTCACATCCTTTTACAACATTGAAATTGTATATCCAGTGCTCGTGATTCTTAAGTGTGATTCTGCAGTTT
ACAGGCTTTGTGTGATGTTA

TAATCNAACCTCGNTNCNGGTTCAGCTGTATNCCATGAGATATGTAATGCGGTGCCGTGCCACATANTCANATCTNGGCA
TNNCNGGGGATCATNGTTCAGATACCGNTGGNATTCTTGACAAGATATCTCCATGCTTCAAGCATGTAATGGTGGGC
AACATGATANTTGGNTCTNCAGTATAGTCGGACAGCCGATGTNNNNNNATCTATACTACCATGACGTCATGAACAGGCA
GGCCCAGGCAAGTAGATAGTNCGGCAGAGACATGTACTTCAACATCGANCATCAGNAGCANACNGAGCGGGCANGAA
NCAGC

Figure 3

```
GAGNNNNGNAACGTTTAGCCTNCCGTAGCCGCCAAAATCCAAGGGNCNACCNACCCTNCG
TTANACTNAATTNGAAAATNCNNNCCCAACTTNAGGNACTTNNAGNCCCCCCNACTTGAC
AACGGAGCACTATATTTACCCCGTGGTNGTTCAACCCAGCCATCTCACCCTTGCGAGCAT
TGGTGCTGCTCTTGATACCCTTCATGCTTAACTATCTCATGATCTTTTACATCATTTTCG
AGTGCATCTGCAACGCCTTTGCGGAACTAAGTTGCTTTGCGGATCGCAACTTTTACGAGG
ATTGGTGGAACTGCGTCAGCTTTGATGAGTGGGCACGCAAATGGAACAAGCCTGTGCAAC
ACTTCTTGCTCCGCCACGTGTACGACTCGAGCATCCGAGTCCTTCCACTTGTCCGAAATC
CAATGCCGCNAATTGCAAACGTTCCTTCCCGGTCGTCAATGCGTTCAACGAACCTGGGTG
AAGAATGGGTGGTGACAACGTTAAAGTGCGCCCGGTATC
```

Figure 4

```
TGGAGGACAACGCGGGGTCTGATACGACTCACTATAGGGAATTTGGCCCTCGAGCAGTAG
ATTCGGCACGATGGGCACGAGGACTCCATCATGTTCCTCAAGCTTTATTCCTACCGGGATG
TCAACCTGTGGTGCCGCCAGCGAAGGGTCAAGGCCAAAGCTGTCTCTACAGGGAAGAAGG
TCAGTGGGGCTGCTGCGAGCAAGCTGTGAGCTATCCAGACAACCTGACCTACCGAGATCTC
GATTACTTCATCTTTGCTCCTACTTTGTGTTATGAACTCAACTTTCCTCGGTCCCCCCGAAT
ACGAGAGCGCTTTCTGCTACGACGAGTTCTTGAGATGCTCTTTTTTACCCAGCTTCAAGTG
GGGCTGATCCAACAGTGGATGGTCCCTACTATCCAGAACTCCATGGAAGCCCTTTCAAGAG
CTTCTGCAGTTTTGGAGACCGCGAGTTCTACAGAGATTGGTGGAATGCTGAGTCTGTCACC
GACTTTTGGCAGAACTGGAATATCCCCGTGG
```

Figure 5

```
CCATGATGGCTCAGGTCCCACTGGCCTGGATTGTGGGCCGATTCTTCCAAGGGAACTATG
GCAATGCAGCTGTGTGGGTGACACTCATCATTGGGCAACCGGTGGCTGTCTCATGTATGTC
CACGACTACTACGTGCTCAACTACGATGCCCCAGTGGGTCATGAGCTACTGCCAAAGGCAG
CCCTCCCTAACCTGGGCCTGGAGTTCTGGAGGGGTTCCTGGCTGCCTGCACACTCCTCCTA
GTCTGGGAGGCCTCTCTGCCCCTATGCGCTACTCCTGCTCTTGGGGATGGCATTTG
```

Figure 6

```
GTCTGGTGTGATGGGGACAGGGAGGGACTTCCCCTTACCCAGCACTGGTGTTGGCTGAGG
TGGGTGCTGAGTCTCAGAGCTTGGCATGGAGACCAGACAGGGCTGGGTCTGCAAGCCTGA
GGCTGCCGCCCTGAGCTCGGGCTGGGACGTGCCCAGAGGTGTTGGGAGGATCTGGGGTG
AGTACCCTGTGGCCAGGACTAAAGGGGCTNCACCCTCCTGTCCATCCCTCGCAGATCTTGA
GCAATGCCCGGTTATTTCTGGAGAACCTCATCAAGTATGGCATCCTGGTGGACCCCATCCA
GGTGGTTTCTCTGTTCCTGAAGGATCCCTATAGCTGGCCCGCCCCATGCCTGGTTATTGCG
GCCAATGTCTTTGCTGTGGCTGCATTCCAGGTTGAGAAGCGCCTGGCGGTGGGTGCCCTG
ACGGAGCAGGCGGGACTGCTGCTGCACGTGGCCAACCTGGCCACCATTCTGTGTTTCCCA
GCGGCTGTGGTCTTACTGGTTGAGTCTATCACTCCAGTGGGCTCCCTGCTGGCGCTGATG
GCGCACACCATCCTCTTCCTCAAGCTCTTCTCCTACCGCGACGTCAACTCATGGTGCCGCA
GGGCCAGGGCCAAGGCTGCCTCTGCAGGGAAGAAGGCCAGCAGTGCTGCTGCCCCGCACA
CCGTGAGCTACCCGGACAATCTGACCTACCGCGATCTCTACTACTTCCTCTTCGCCCCCACC
TTGTGCTACGAGCTCAACTTTCCCCGCTCTCCCCGCATCCGGAAGCGCTTTCTGCTGCGAC
GGATCCTTGAGATGCTGTTCTTCACCCAGCTCCAGGTGGGGCTGATCCAGCAGTGGATGG
TCCCCACCATCCAGAACTCCATGAAGCCCTTCAAGGACATGGACTACTCACGCATCATCGA
GCGCCTCCTGAAGCTGGCGGTCCCCAATCACCTCATCTGGCTCATCTTCTTCTACTGGCTC
TTCCACTCCTGCCTGAATGCCGTGGCTGAGCTCATGCAGTTTGGAGACCGGGAGTTCTACC
GGGACTGGTGGAACTCCGAGTCTGTCACCTACTTCTGGCAGAACTGGAACATCCCTGTGCA
CAAGTGGTGCATCAGACACTTCTACAAGCCCATGCTTCGACGGGGCAGCAGCAAGTGGAT
GGCCAGGACAGGGGTGTTCCTGGCCTCGGCCTTCTTCCACGAGTACCTGGTGAGCGTCCC
TCTGCGAATGTTCCGCCTCTGGGCGTTCACGGGCATGATGGCTCAGATCCCACTGGCCTG
GTTCGTGGGCCGCTTTTTCCAGGGCAACTATGGCAACGCAGCTGTGTGGCTGTCGCTCATC
ATCGGACAGCCAATAGCCGTCCTCATGTACGTCCACGACTACTACGTGCTCAACTATGAGG
CCCCAGCGGCAGAGGCCTGAGCTGCACCTGAGGGCCTGGCTTCTCACTGCCACCTCACACC
CGCTGCCAGAGCCCACCTCTCCTCCTAGGCCTCGAGTGCTGGGGATGGGCCTGGCTGCAC
AGCATCCTCCTCTGGTCCCAGGGAGGCCTCTCTGCCCCTATGGGGCTCTGTCCTGCACCCC
TCAGGGATGGCGACAGCAGGCCAGACACAGTCTGATGCCAGCTGGGAGTCTTGCTGACCC
TGCCCCGGGTCCGAGGGTGTCAATAAAGTGCTGTCCAGTGACCTCTTCAGCCTGCCAGGG
GCCTGGGGCCTGGTGGGGGGTATGGCCACACCCACAAGGGCGAGTGCCAGAGCTGTGTG
GACAGCTGTCCCAGGACCTGCCGGGGAGCAGCAGCTCCACTGCAGCAGGGCGGGCATGGC
CGGTAGGGGGAGTGCAAGGCCAGGCAGACGCCCCCATTCCCCACACTCCCCTACCTAGAAA
AGCTCAGCTCAGGCGTCCTCT
```

Figure 7

```
CACGACTGGGCCGCGACGTGGTGCGGGCCGAAGCCATGGGCGACCGCGGAGGCGCGGGA
AGCTCTCGGCGTCGGAGGACCGGCTCGCGGGTTTCCATCCAGGGTGGTAGTGGGCCCATG
GTAGACGAAGAGGAGGTGCGAGACGCCGCTGTGGGCCCCGACTTGGGCGCCGGGGGTGA
CGCTCCGGCTCCGGCTCCGGTTCCGGCTCCAGCCCACACCCGGGACAAAGACCGGCAGAC
CAGCGTGGGCGACGGCCACTGGGAGCTGAGGTGCCATCGTCTGCAAGACTCTTTGTTCAG
CTCAGACAGCGGTTTCAGCAATTACCGTGGTATCCTGAATTGGTGCGTGGTGATGCTGATC
CTGAGTAATGCAAGGTTATTTTTAGAGAATCTTATCAAGTATGGCATCCTGGTGGATCCCA
TCCAGGTGGTGTCTCTGTTTCTGAAGGACCCCTACAGCTGGCCTGCCCCATGCTTGATCAT
TGCATCCAATATCTTTATTGTGGCTACATTTCAGATTGAGAAGCGCCTGTCAGTGGGTGCC
CTGACAGAGCAGATGGGGCTGCTGCTACATGTGGTTAACCTGGCCACAATTATCTGCTTCC
CAGCAGCTGTGGCCTTACTGGTTGAGTCTATCACTCCAGTGGGTTCCCTGTTTGCTCTGGC
ATCATACTCCATCATCTTCCTCAAGCTTTTCTCCTACCGGGATGTCAATCTGTGGTGCCGCC
AGCGAAGGGTCAAGGCCAAAGCTGTGTCTGCAGGGAAGAAGGTCAGTGGGGCTGCTGCCC
AGAACACTGTAAGCTATCCGGACAACCTGACCTACCGAGATCTCTATTACTTCATCTTTGCT
CCTACTTTGTGTTATGAACTCAACTTTCCTCGATCCCCCCGAATACGAAAGCGCTTTCTGCT
ACGGCGGGTTCTTGAGATGCTCTTTTTCACCCAGCTTCAAGTGGGGCTGATCCAGCAGTGG
ATGGTCCCTACTATCCAGAACTCCATGAAGCCCTTCAAGGACATGGACTATTCACGAATCAT
TGAGCGTCTCTTAAAGCTGGCGGTCCCCAACCATCTGATATGGCTCATCTTCTTCTATTGG
CTTTTCCACTCATGTCTCAATGCTGTGGCAGAGCTCCTGCAGTTTGGAGACCGCGAGTTCT
ACAGGGACTGGTGGAATGCTGAGTCTGTCACCTACTTTTGGCAGAACTGGAATATCCCCGT
GCACAAGTGGTGCATCAGACACTTCTACAAGCCTATGCTCAGACTGGGCAGCAACAAATGG
ATGGCCAGGACTGGGGTCTTTTTGGCGTCAGCCTTCTTCCATGAGTACCTAGTGAGCATTC
CCCTGAGGATGTTCCGCCTCTGGGCATTCACAGCCATGATGGCTCAGGTCCCACTGGCCTG
GATTGTGAACCGCTTCTTCCAAGGGAACTATGGCAATGCAGCTGTGTGGGTGACACTCATC
ATTGGGCAACCGGTGGCTGTGCTCATGTATGTCCACGACTACTACGTGCTCAACTATGATG
CCCCAGTGGGGGCCTGAGCTACTGCCAAAGGCCAGCCCTCCCTAACCTGGGCCTGGAGTT
CTGGAGGGCTTCCTGGCTGCCTGCACACTCCTCCTAGTCTGGGAGGCCTCTCTGCCCCTAT
GGGGCCTACTCCTGCTCTTGGGGATGGCACCTGAGTCCAGCTGGTATGAGCCAGTGCTGG
GAGTCTGTGCTGACCAGGGGCTGAGGATATCAATAAAGAGCTATCTAAAAAAAAAAAAAAA
AAA
```

Figure 8

```
CACGACTGGGCCGCGACGTGGTGCGGGCCGAAGCCATGGGCGACCGCGGAGGCGCGGGA
AGCTCTCGGCGTCGGAGGACCGGCTCGCGGGTTTCCATCCAGGGTGGTAGTGGGCCCATG
GTAGACGAAGAGGAGGTGCGAGACGCCGCTGTGGGCCCCGACTTGGGCGCCGGGGGTGA
CGCTCCGGCTCCGGCTCCGGTTCCGGCTCCAGCCCACACCCGGGACAAAGACCGGCAGAC
CAGCGTGGGCGACGGCCACTGGGAGCTGAGGTGCCATCGTCTGCAAGACTCTTTGTTCAG
CTCAGACAGCGGTTTCAGCAATTACCGTGGTATCCTGAATTGGTGCGTGGTGATGCTGATC
CTGAGTAATGCAAGGTTATTTTTAGAGAATCTTATCAAGTATGGCATCCTGGTGGATCCCA
TCCAGGTGGTGTCTCTGTTTCTGAAGGACCCCTACAGCTGGCCTGCCCCATGCTTGATCAT
TGCATCCAATATCTTTATTGTGGCTACATTTCAGATTGAGAAGCGCCTGTCAGTGGGTGCC
CTGACAGAGCAGATGGGGCTGCTGCTACATGTGGTTAACCTGGCCACAATTATCTGCTTCC
CAGCAGCTGTGGCCTTACTGGTTGAGTCTATCACTCCAGTGGGTTCCCTGTTTGCTCTGGC
ATCATACTCCATCATCTTCCTCAAGCTTTTCTCCTACCGGGATGTCAATCTGTGGTGCCGCC
AGCGAAGGGTCAAGGCCAAAGCTGTGTCTGCAGGGAAGAAGGTCAGTGGGGCTGCTGCCC
AGAACACTGTAAGCTATCCGGACAACCTGACCTACCGAGATCTCTATTACTTCATCTTTGCT
CCTACTTTGTGTTATGAACTCAACTTTCCTCGATCCCCCCGAATACGAAAGCGCTTTCTGCT
ACGGCGGGTTCTTGAGATGCTCTTTTTCACCCAGCTTCAAGTGGGGCTGATCCAGCAGTGG
ATGGTCCCTACTATCCAGAACTCCATGAAGCCCTTCAAGGACATGGACTATTCACGAATCAT
TGAGCGTCTCTTAAAGCTGGCGGTCCCCAACCATCTGATATGGCTCATCTTCTTCTATTGG
CTTTTCCACTCATGTCTCAATGCTGTGGCAGAGCTCCTGCAGTTTGGAGACCGCGAGTTCT
ACAGGGACTGGTGGAATGCTGAGTCTGTCACCTACTTTTGGCAGAACTGGAATATCCCCGT
GCACAAGTGGTGCATCAGACACTTCTACAAGCCTATGCTCAGACTGGGCAGCAACAAATGG
ATGGCCAGGACTGGGGTCTTTTTGGCGTCAGCCTTCTTCCATGAGTACCTAGTGAGCATTC
CCCTGAGGATGTTCCGCCTCTGGGCATTCACAGCCATGATGGCTCAGGTCCCACTGGCCTG
GATTGTGAACCGCTTCTTCCAAGGGAACTATGGCAATGCAGCTGTGTGGGTGACACTCATC
ATTGGGCAACCGGTGGCTGTGCTCATGTATGTCCACGACTACTACGTGCTCAACTATGATG
CCCCAGTGGGGGCCTGAGCTACTGCCAAAGGCCAGCCCTCCCTAACCTGGGCCTGGAGTT
CTGGAGGGCTTCCTGGCTGCCTGCACACTCCTCCTAGTCTGGGAGGCCTCTCTGCCCCTAT
GGGGCCTACTCCTGCTCTTGGGGATGGCACCTGAGTCCAGCTGGTATGAGCCAGTGCTGG
GAGTCTGTGCTGACCAGGGGCTGAGGATATCAATAAAGAGCTATCTAAAAAAAAAAAAAAA
AAA
```

Figure 10

MGDRGGAGSSRRRRTGSRVSIQGGSGPMVDEEEVRDAAVGPDLGAGGDAPAPAPVPAPAHT
RDKDRQTSVGDGHWELRCHRLQDSLFSSDSGFSNYRGILNWCVVMLILSNARLFLENLIKYGI
LVDPIQVVSLFLKDPYSWPAPCLIIASNIFIVATFQIEKRLSVGALTEQMGLLLHVVNLATIICFP
AAVALLVESITPVGSLFALASYSIIFLKLFSYRDVNLWCRQRRVKAKAVSAGKKVSGAAAQNTV
SYPDNLTYRDLYYFIFAPTLCYELNFPRSPRIRKRFLLRRVLEMLFFTQLQVGLIQQWMVPTIQ
NSMKPFKDMDYSRIIERLLKLAVPNHLIWLIFFYWLFHSCLNAVAELLQFGDREFYRDWWNAE
SVTYFWQNWNIPVHKWCIRHFYKPMLRLGSNKWMARTGVFLASAFFHEYLVSIPLRMFRLW
AFTAMMAQVPLAWIVNRFFQGNYGNAAVWVTLIIGQPVAVLMYVHDYYVLNYDAPVGA

Figure 11

MRQQTGRRRRQPSETSNGSLASSRRSSFAQNGNSSRKSSEMRGPCEKVVHTAQDSLFSTSS
GWTNFRGFFNLSILLLVLSNGRVALENVIKYGILITPLQWISTFVEHHYSIWSWPNLALILCSNI
QILSVFGMEKILERGWLGNGFAAVFYTSLVIAHLTIPVVVTLTHKWKNPLWSVVMMGVYVIEA
LKFISYGHVNYWARDARRKITELKTQVTDLAKKTCDPKQFWDLKDELSMHQMAAQYPANLTL
SNIYYFMAAPTLCYEFKFPRLLRIRKHFLIKRTVELIFLSFLIAALVQQWVVPTVRNSMKPLSEM
EYSRCLERLLKLAIPNHLIWLLFFYTFFHSFLNLIAELLRFADREFYRDFWNAETIGYFWKSWNI
PVHRFAVRHIYSPMMRNNFSKMSAFFVVFFVSAFFHEYLVSVPLKIFRLWSYYGMMGQIPLSII
TDKVVRGGRTGNIIVWLSLIVGQPLAILMYGHDWYILNFGVSAVQNQTVGI

Figure 12

TTTGATATGTACGGTAAATGGAAAAAAGGTATTCATGTATGGCAAGGTGGTAATAAATGGC
ACTAAATATGTTTCAAAAGTGTGAGCAAACGTATGTGAGAGACGAGAAAAATAAGAAAACG
ACCTGTAATACATGAAAAATATCAATAGGAATTTTGAGATAATTTGGCAACATGCAATATAA
TGATTATAATAAAAAACTTGTCTTAAGACTAGAGAACTGCTAATTCAAAAAAAACAAATTGA
GATAAATCAAATACCAACGGTTTGGTTTTGAACTGCTGAAACACCAAAGTTCAA

Figure 13

TGCAAATGCGTCAACAAACGGGACGACGGCGGCGTCAGCCTTCGGNAAACATCTAATGGT
TCTTTGGCTTCCAGTAGACGCTCCTCATTTGCACAAAATGGTAATTCGTCAAGGGAAAAGT
TCAGAAATGAGAGGACCTTGCGAGAAAGTGGTACATACTGCTCAAGATTCATTGTTTTCGA
CGAGTTCTGGATGGACAAATTTCCGTGGATTCTTCAATTTGTCTATTTTACTTTTGGTACTT
TCAAATGGACGCGTGGCACTTGAAAATGTGATCAAATATGGTATTTTGATAACACCCCTTC
AGTGGATCTCAACGTTTGTTGAGCATCACTACTCAATTTGGAGCTGGCCAAATCTTGCTCT
CATCCTATGCTCAAA

Figure 14

SEQUENCE LISTING

<160> NUMBER OF SEQ ID NOS: 46

<210> SEQ ID NO 1
<211> LENGTH: 1942
<212> TYPE: DNA
<213> ORGANISM: Arabidopsis thaliana

<400> SEQUENCE: 1

| | | | | | |
|---|---|---|---|---|---:|
| ctctcgtgaa | tcctttttcc | tttcttcttc | ttcttctctt | cagagaaaac | tttgcttctc | 60 |
| tttctataag | gaaccagaca | cgaatcccat | tcccaccgat | ttcttagctt | cttccttcaa | 120 |
| tccgctcttt | ccctctccat | tagattctgt | ttcctctttc | aatttcttct | gcatgcttct | 180 |
| cgattctctc | tgacgcctct | tttctcccga | cgctgtttcg | tcaaacgctt | ttcgaaatgg | 240 |
| cgattttgga | ttctgctggc | gttactacgg | tgacggagaa | cggtggcgga | gagttcgtcg | 300 |
| atcttgatag | gcttcgtcga | cggaaatcga | gatcggattc | ttctaacgga | cttcttctct | 360 |
| ctggttccga | taataattct | ccttcggatg | atgttggagc | tcccgccgac | gttagggatc | 420 |
| ggattgattc | cgttgttaac | gatgacgctc | agggaacagc | caatttggcc | ggagataata | 480 |
| acggtggtgg | cgataataac | ggtggtggaa | gaggcggcgg | agaaggaaga | ggaaacgccg | 540 |
| atgctacgtt | tacgtatcga | ccgtcggttc | cagctcatcg | gagggcgaga | gagagtccac | 600 |
| ttagctccga | cgcaatcttc | aaacagagcc | atgccggatt | attcaacctc | tgtgtagtag | 660 |
| ttcttattgc | tgtaaacagt | agactcatca | tcgaaaatct | tatgaagtat | ggttggttga | 720 |
| tcagaacgga | tttctggttt | agttcaagat | cgctgcgaga | ttggccgctt | ttcatgtgtt | 780 |
| gtatatccct | ttcgatcttt | cctttggctg | cctttacggt | tgagaaattg | gtacttcaga | 840 |
| aatacatatc | agaacctgtt | gtcatctttc | ttcatattat | tatcaccatg | acagaggttt | 900 |
| tgtatccagt | ttacgtcacc | ctaaggtgtg | attctgcttt | tttatcaggt | gtcactttga | 960 |
| tgctcctcac | ttgcattgtg | tggctaaagt | tggtttctta | tgctcatact | agctatgaca | 1020 |
| taagatccct | agccaatgca | gctgataagg | ccaatcctga | agtctcctac | tacgttagct | 1080 |
| tgaagagctt | ggcatatttc | atggtcgctc | ccacattgtg | ttatcagcca | agttatccac | 1140 |
| gttctgcatg | tatacggaag | ggttgggtgg | ctcgtcaatt | tgcaaaactg | gtcatattca | 1200 |
| ccggattcat | gggatttata | atagaacaat | atataaatcc | tattgtcagg | aactcaaagc | 1260 |
| atcctttgaa | aggcgatctt | ctatatgcta | ttgaaagagt | gttgaagctt | tcagttccaa | 1320 |
| atttatatgt | gtggctctgc | atgttctact | gcttcttcca | cctttggtta | aacatattgg | 1380 |
| cagagcttct | ctgcttcggg | gatcgtgaat | tctacaaaga | ttggtggaat | gcaaaaagtg | 1440 |
| tgggagatta | ctggagaatg | tggaatatgc | ctgttcataa | atggatggtt | cgacatatat | 1500 |
| acttcccgtg | cttgcgcagc | aagataccaa | agacactcgc | cattatcatt | gctttcctag | 1560 |
| tctctgcagt | ctttcatgag | ctatgcatcg | cagttccttg | tcgtctcttc | aagctatggg | 1620 |
| cttttcttgg | gattatgttt | caggtgcctt | tggtcttcat | cacaaactat | ctacaggaaa | 1680 |
| ggtttggctc | aacggtgggg | aacatgatct | tctggttcat | cttctgcatt | ttcggacaac | 1740 |
| cgatgtgtgt | gcttctttat | taccacgacc | tgatgaaccg | aaaaggatcg | atgtcatgaa | 1800 |
| acaactgttc | aaaaaatgac | tttcttcaaa | catctatggc | ctcgtggat | ctccgttgat | 1860 |
| gttgtggtgg | ttctgatgct | aaaacgacaa | atagtgttat | aaccattgaa | gaagaaaga | 1920 |
| caattagagt | tgttgtatcg | ca | | | | 1942 |

```
<210> SEQ ID NO 2
<211> LENGTH: 520
<212> TYPE: PRT
<213> ORGANISM: Arabidopsis thaliana

<400> SEQUENCE: 2
```

| | | | | | | | | | | | | | | | |
|---|---|---|---|---|---|---|---|---|---|---|---|---|---|---|---|
| Met | Ala | Ile | Leu | Asp | Ser | Ala | Gly | Val | Thr | Thr | Val | Thr | Glu | Asn | Gly |
| 1 | | | | 5 | | | | | 10 | | | | | 15 | |
| Gly | Gly | Glu | Phe | Val | Asp | Leu | Asp | Arg | Leu | Arg | Arg | Arg | Lys | Ser | Arg |
| | | | 20 | | | | | 25 | | | | | 30 | | |
| Ser | Asp | Ser | Ser | Asn | Gly | Leu | Leu | Leu | Ser | Gly | Ser | Asp | Asn | Asn | Ser |
| | | 35 | | | | | 40 | | | | | 45 | | | |
| Pro | Ser | Asp | Asp | Val | Gly | Ala | Pro | Asp | Val | Arg | Asp | Arg | Ile | Asp | |
| | 50 | | | | | 55 | | | | | 60 | | | | |
| Ser | Val | Val | Asn | Asp | Asp | Ala | Gln | Gly | Thr | Ala | Asn | Leu | Ala | Gly | Asp |
| 65 | | | | | 70 | | | | | 75 | | | | | 80 |
| Asn | Asn | Gly | Gly | Gly | Asp | Asn | Asn | Gly | Gly | Gly | Arg | Gly | Gly | Gly | Glu |
| | | | | 85 | | | | | 90 | | | | | 95 | |
| Gly | Arg | Gly | Asn | Ala | Asp | Ala | Thr | Phe | Thr | Tyr | Arg | Pro | Ser | Val | Pro |
| | | | 100 | | | | | 105 | | | | | 110 | | |
| Ala | His | Arg | Arg | Ala | Arg | Glu | Ser | Pro | Leu | Ser | Ser | Asp | Ala | Ile | Phe |
| | | 115 | | | | | 120 | | | | | 125 | | | |
| Lys | Gln | Ser | His | Ala | Gly | Leu | Phe | Asn | Leu | Cys | Val | Val | Val | Leu | Ile |
| 130 | | | | | 135 | | | | | 140 | | | | | |
| Ala | Val | Asn | Ser | Arg | Leu | Ile | Ile | Glu | Asn | Leu | Met | Lys | Tyr | Gly | Trp |
| 145 | | | | | 150 | | | | | 155 | | | | | 160 |
| Leu | Ile | Arg | Thr | Asp | Phe | Trp | Phe | Ser | Ser | Arg | Ser | Leu | Arg | Asp | Trp |
| | | | | 165 | | | | | 170 | | | | | 175 | |
| Pro | Leu | Phe | Met | Cys | Cys | Ile | Ser | Leu | Ser | Ile | Phe | Pro | Leu | Ala | Ala |
| | | | 180 | | | | | 185 | | | | | 190 | | |
| Phe | Thr | Val | Glu | Lys | Leu | Val | Leu | Gln | Lys | Tyr | Ile | Ser | Glu | Pro | Val |
| | | | 195 | | | | | 200 | | | | | 205 | | |
| Val | Ile | Phe | Leu | His | Ile | Ile | Ile | Thr | Met | Thr | Glu | Val | Leu | Tyr | Pro |
| | 210 | | | | | 215 | | | | | 220 | | | | |
| Val | Tyr | Val | Thr | Leu | Arg | Cys | Asp | Ser | Ala | Phe | Leu | Ser | Gly | Val | Thr |
| 225 | | | | | 230 | | | | | 235 | | | | | 240 |
| Leu | Met | Leu | Leu | Thr | Cys | Ile | Val | Trp | Leu | Lys | Leu | Val | Ser | Tyr | Ala |
| | | | | 245 | | | | | 250 | | | | | 255 | |
| His | Thr | Ser | Tyr | Asp | Ile | Arg | Ser | Leu | Ala | Asn | Ala | Ala | Asp | Lys | Ala |
| | | | 260 | | | | | 265 | | | | | 270 | | |
| Asn | Pro | Glu | Val | Ser | Tyr | Tyr | Val | Ser | Leu | Lys | Ser | Leu | Ala | Tyr | Phe |
| | | 275 | | | | | 280 | | | | | 285 | | | |
| Met | Val | Ala | Pro | Thr | Leu | Cys | Tyr | Gln | Pro | Ser | Tyr | Pro | Arg | Ser | Ala |
| | 290 | | | | | 295 | | | | | 300 | | | | |
| Cys | Ile | Arg | Lys | Gly | Trp | Val | Ala | Arg | Gln | Phe | Ala | Lys | Leu | Val | Ile |
| 305 | | | | | 310 | | | | | 315 | | | | | 320 |
| Phe | Thr | Gly | Phe | Met | Gly | Phe | Ile | Ile | Glu | Gln | Tyr | Ile | Asn | Pro | Ile |
| | | | | 325 | | | | | 330 | | | | | 335 | |
| Val | Arg | Asn | Ser | Lys | His | Pro | Leu | Lys | Gly | Asp | Leu | Leu | Tyr | Ala | Ile |
| | | | 340 | | | | | 345 | | | | | 350 | | |
| Glu | Arg | Val | Leu | Lys | Leu | Ser | Val | Pro | Asn | Leu | Tyr | Val | Trp | Leu | Cys |
| | | 355 | | | | | 360 | | | | | 365 | | | |
| Met | Phe | Tyr | Cys | Phe | Phe | His | Leu | Trp | Leu | Asn | Ile | Leu | Ala | Glu | Leu |
| | 370 | | | | | 375 | | | | | 380 | | | | |

```
Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
                500                 505                 510

Met Asn Arg Lys Gly Ser Met Ser
        515                 520

<210> SEQ ID NO 3
<211> LENGTH: 234
<212> TYPE: DNA
<213> ORGANISM: Glycine max
<220> FEATURE:
<221> NAME/KEY: misc_feature
<222> LOCATION: (24)..(60)
<223> OTHER INFORMATION: n at positions 24, 41, and 60 is unknown

<400> SEQUENCE: 3
gtaagcttca agagcttagc atanttcctg gttgccccta ncattatgtt accagccaan      60
ctatcctcgc acaccttata ttcgaaaggg ttggctgttt cgccaacttg tcaactgata    120
atatttacag gagttatggg atttataata gaacaataca ttaatcccat tgtacaaaat    180
tcacagcatc ctctcaaggg aaaccttctt tacgccatcg agagagttct gaag          234

<210> SEQ ID NO 4
<211> LENGTH: 267
<212> TYPE: DNA
<213> ORGANISM: Glycine max

<400> SEQUENCE: 4
ctgcttttgt atctggtgtc acgttgatgc tattaacttg cattgtgtgg ttaaaattgg     60
tgtcatatgc acatacaaac tatgatatga gagcacttac tgtttcgaat gaaaagggag   120
aaacattacc caatactttg atatggagta ccgtacact gtgaccttca ggagtttggc    180
atacttcatg gttgctccta cattatgcta tcagacaagc tatcctcgca caccttcagt   240
tcgaaagggt tgggtgtttc gtcaact                                         267

<210> SEQ ID NO 5
<211> LENGTH: 275
<212> TYPE: DNA
<213> ORGANISM: Glycine max
<220> FEATURE:
<221> NAME/KEY: misc_feature
<222> LOCATION: (192)..(263)
<223> OTHER INFORMATION: n at positions 192, 202, 204, 211, 222, 234,
      238, 239, 244, 245, 247, 251, 262, and 263 is unknown
```

<400> SEQUENCE: 5

| gtggaatgcc aaaactgttg aagattattg gaggatgtgg aatatgcctg ttcacaaatg | 60 |
| gatgatccgc cacctatatt ttccatgttt aaggcacggt ataccaaagg ccgttgctct | 120 |
| tttaattgcc ttcctggttc tgctttattc catgagctgc gcatcgctgt tccttgccca | 180 |
| catattcaag tngtgggttt cngnggaatt nagtttcagg tnccttgggt ttcnaccnna | 240 |
| attnntnggc naaaaaattc cnngaaccccc ggggg | 275 |

<210> SEQ ID NO 6
<211> LENGTH: 257
<212> TYPE: DNA
<213> ORGANISM: Glycine max

<400> SEQUENCE: 6

| aacggaattg agactccaga gaatatgcca aaatgtatta ataattgtca caacttggaa | 60 |
| ggcttttgga aaaactggca tgcttccttc aacaagtggc ttgtgaggta tatatacatt | 120 |
| cctcttgggg gatctaagaa aaagctacta aatgtgtggg ttgttttcac atttgttgca | 180 |
| atctggcatg atttagagtg gaagcttctt tcatgggcat ggttgacgtg tttattcttc | 240 |
| atccctgagt tggtttt | 257 |

<210> SEQ ID NO 7
<211> LENGTH: 253
<212> TYPE: DNA
<213> ORGANISM: Zea mays

<400> SEQUENCE: 7

| agaaaatgga acatgcctgt gcataaatgg attgttcgtc atatatattt tccttgcatg | 60 |
| cgaaatggta tatcaaagga agttgctgtt tttatatcgt tcttgtttct gctgtacttc | 120 |
| atgagttatg tgttgctgtt ccctgccaca tactcaagtt ctgggctttt tttaggaatc | 180 |
| atgcttcaga ttcccctcat catattgaca tcatacctca aaaataaatt cagtgacaca | 240 |
| atggttggca ata | 253 |

<210> SEQ ID NO 8
<211> LENGTH: 254
<212> TYPE: DNA
<213> ORGANISM: Zea mays

<400> SEQUENCE: 8

| tgaagtatgg cttattaata agatctggct tttggtttaa tgctacatca ttgcgagact | 60 |
| ggccactgct aatgtgttgc cttagtctac ccatatttcc ccttggtgca tttgcagtcg | 120 |
| aaaagttggc attcaacaat ctcattagtg atcctgctac tacctgtttt cacatcctttt | 180 |
| ttacaacatt tgaaattgta tatccagtgc tcgtgattct taagtgtgat tctgcagttt | 240 |
| tatcaggctt tgtg | 254 |

<210> SEQ ID NO 9
<211> LENGTH: 262
<212> TYPE: DNA
<213> ORGANISM: Zea mays

<400> SEQUENCE: 9

| gaagtatggc ttattaataa gatctggctt ttggtttaat gctacatcat tgcgagactg | 60 |
| gccactgcta atgtgttgcc ttagtctacc catatttccc cttggtgcat ttgcagtcga | 120 |
| aaagttggca ttcaacaatc tcattagtga tcctgctact acctgttttc acatcctttt | 180 |

```
tacaacattt gaaattgtat atccagtgct cgtgattctt aagtgtgatt ctgcagtttt    240
acaggctttg tgttgatgtt ta                                              262

<210> SEQ ID NO 10
<211> LENGTH: 325
<212> TYPE: DNA
<213> ORGANISM: Zea mays
<220> FEATURE:
<221> NAME/KEY: misc_feature
<222> LOCATION: (6)..(321)
<223> OTHER INFORMATION: n at positions 6, 14, 16, 18, 32, 67, 71, 76,
      82, 83, 85, 94, 107, 111, 170, 176, 180, 204, 205, 206, 207, 208,
      209, 261, 289, 296, 301, 304, 317, and 321  is unknown

<400> SEQUENCE: 10
taatcnaacc tcgntncngg ttcagctgta tnccatgaga tatgtaatgc ggtgccgtgc    60
cacatantca natctnggca tnncnggat  catngttcag ataccgntgg nattcttgac    120
aagatatctc catgctacgt tcaagcatgt aatggtgggc aacatgatan tttggntctn    180
cagtatagtc ggacagccga tgtnnnnnna tctatactac catgacgtca tgaacaggca    240
ggcccaggca agtagatagt ncggcagaga catgtacttc aacatcganc atcagnagca    300
nacngagcga gcggcangaa ncagc                                          325

<210> SEQ ID NO 11
<211> LENGTH: 519
<212> TYPE: DNA
<213> ORGANISM: Mortierella alpina
<220> FEATURE:
<221> NAME/KEY: misc_feature
<222> LOCATION: (4)..(430)
<223> OTHER INFORMATION: n at positions
      4,5,6,7,9,22,46,48,52,58,64,68,73,80,82,83,84,93
      97,102,103,106,113,148,430 is unknown

<400> SEQUENCE: 11
gagnnnngna acgtttagcc tnccgtagcc gccaaaatcc aagggncnac cnaccctncg    60
ttanactnaa ttngaaaatn cnnncccaac ttnaggnact tnnagncccc ccnacttgac    120
aacggagcac tatatttacc ccgtggtngt tcaacccagc catctcaccc ttgcgagcat    180
tggtgctgct cttgataccc ttcatgctta actatctcat gatcttttac atcattttcg    240
agtgcatctg caacgccttt gcggaactaa gttgctttgc ggatcgcaac ttttacgagg    300
attggtggaa ctgcgtcagc tttgatgagt gggcacgcaa atggaacaag cctgtgcaac    360
acttcttgct ccgccacgtg tacgactcga gcatccgagt ccttccactt gtccgaaatc    420
caatgccgcn aattgcaaac gttccttccc ggtcgtcaat gcgttcaacg aacctgggtg    480
aagaatgggt ggtgacaacg ttaaagtgcg cccggtatc                           519

<210> SEQ ID NO 12
<211> LENGTH: 518
<212> TYPE: DNA
<213> ORGANISM: murine

<400> SEQUENCE: 12
tggaggacaa cgcggggtct gatacgactc actataggga atttggccct cgagcagtag    60
attcggcacg atgggcacga ggactccatc atgttcctca agctttattc ctaccgggat    120
gtcaacctgt ggtgccgcca gcgaagggtc aaggccaaag ctgtctctac agggaagaag    180
gtcagtgggg ctgctgcgag caagctgtga gctatccaga caacctgacc taccgagatc    240
tcgattactt catctttgct cctactttgt gttatgaact caactttcct cggtcccccc    300
```

```
gaatacgaga gcgctttctg ctacgacgag ttcttgagat gctctttttt acccagcttc    360
aagtggggct gatccaacag tggatggtcc ctactatcca gaactccatg gaagcccttt    420
caagagcttc tgcagttttg gagaccgcga gttctacaga gattggtgga atgctgagtc    480
tgtcaccgac ttttggcaga actggaatat ccccgtgg                            518
```

<210> SEQ ID NO 13
<211> LENGTH: 299
<212> TYPE: DNA
<213> ORGANISM: murine

<400> SEQUENCE: 13

```
ccatgatggc tcaggtccca ctggcctgga ttgtgggccg attcttccaa gggaactatg     60
gcaatgcagc tgtgtgggtg acactcatca ttgggcaacc ggtggctgtc tcatgtatgt    120
ccacgactac tacgtgctca actacgatgc cccagtgggt catgagctac tgccaaaggc    180
agccctccct aacctgggcc tggagttctg gaggggttcc tggctgcctg cacactcctc    240
ctagtctggg aggcctctct gccctatgc gctactcctg ctcttgggga tggcatttg     299
```

<210> SEQ ID NO 14
<211> LENGTH: 1895
<212> TYPE: DNA
<213> ORGANISM: Human
<220> FEATURE:
<221> NAME/KEY: misc_feature
<222> LOCATION: (209)
<223> OTHER INFORMATION: n at position 209 is unknown

<400> SEQUENCE: 14

```
gtctggtgtg atggggacag ggagggactt cccttaccc agcactggtg ttggctgagg     60
tgggtgctga gtctcagagc ttggcatgga gaccagacag ggctgggtct gcaagcctga    120
ggctgccgcc ctgagctcgg gctgggacgt gcccagaggt gttgggagga tctgggtga    180 gtaccctgtg ccaggactaa aggggctnc accctcctgt ccatccctcg cagatcttga    240
gcaatgcccg ttatttctg agaacctca tcaagtatgg catcctggtg accccatcc      300 aggtggtttc tctgttcctg aaggatccct atagctggcc cgcccatgc ctggttattg    360 cggccaatgt ctttgctgtg gctgcattcc aggttgagaa cgcctggcg gtgggtgccc    420 tgacggagca ggcgggactg ctgctgcacg tggccaacct ggccaccatt ctgtgtttcc    480
cagcggctgt ggtcttactg gttgagtcta tcactccagt gggctccctg ctggcgctga    540
tggcgcacac catcctcttc ctcaagctct ctcctaccg cgacgtcaac tcatggtgcc    600
gcagggccag ggccaaggct gcctctgcag ggaagaaggc cagcagtgct gctgccccgc    660
acaccgtgag ctacccggac aatctgacct accgcgatct ctactacttc ctcttcgccc    720
ccaccttgtg ctacgagctc aactttcccc gctctccccg catccggaag cgctttctgc    780
tgcgacggat ccttgagatg ctgttcttca cccagctcca ggtggggctg atccagcagt    840
ggatggtccc caccatccag aactccatga gcccttcaa ggacatggac tactcacgca    900
tcatcgagcg cctcctgaag ctggcggtcc caatcacct catctggctc atcttcttct    960
actggctctt ccactcctgc ctgaatgccg tgctgagct catgcagttt ggagaccggg    1020
agttctaccg ggactggtgg aactccgagt ctgtcaccta cttctggcag aactggaaca   1080
tccctgtgca agtggtgc atcagacact tctacaagcc catgcttcga cggggcagca   1140
gcaagtggat ggccaggaca gggtgttcc tggcctcggc cttcttccac gagtacctgg   1200
tgagcgtccc tctgcgaatg ttccgcctct gggcgttcac gggcatgatg gctcagatcc   1260
```

```
cactggcctg gttcgtgggc cgcttttttcc agggcaacta tggcaacgca gctgtgtggc   1320
tgtcgctcat catcggacag ccaatagccg tcctcatgta cgtccacgac tactacgtgc   1380
tcaactatga ggccccagcg gcagaggcct gagctgcacc tgagggcctg gcttctcact   1440
gccacctcac acccgctgcc agagcccacc tctcctccta ggcctcgagt gctggggatg   1500
ggcctggctg cacagcatcc tcctctggtc cagggaggc ctctctgccc ctatggggct    1560
ctgtcctgca cccctcaggg atggcgacag caggccagac acagtctgat gccagctggg   1620
agtcttgctg accctgcccc gggtccgagg gtgtcaataa agtgctgtcc agtgacctct   1680
tcagcctgcc aggggcctgg ggcctggtgg ggggtatggc cacacccaca agggcgagtg   1740
ccagagctgt gtggacagct gtcccaggac ctgccgggga gcagcagctc cactgcagca   1800
gggcgggcat ggccggtagg gggagtgcaa ggccaggcag acgcccccat tccccacact   1860
cccctaccta gaaaagctca gctcaggcgt cctct                              1895
```

<210> SEQ ID NO 15
<211> LENGTH: 1766
<212> TYPE: DNA
<213> ORGANISM: Rattus sp.

<400> SEQUENCE: 15

```
cacgactggg ccgcgacgtg gtgcgggccg aagccatggg cgaccgcgga ggcgcgggaa     60
gctctcggcg tcggaggacc ggctcgcggg tttccatcca gggtggtagt gggcccatgg    120
tagacgaaga ggaggtgcga gacgccgctg tgggcgccga cttgggcgcc gggggtgacg    180
ctccggctcc ggctccggtt ccggctccag cccacacccg ggacaaagac cggcagacca    240
gcgtgggcga cggccactgg gagctgaggt gccatcgtct gcaagactct tgttcagct    300 cagacagcgg tttcagcaat taccgtggta tcctgaattg gtgcgtggtg atgctgatcc    360
tgagtaatgc aaggttattt ttagagaatc ttatcaagta tggcatcctg gtggatccca    420
tccaggtggt gtctctgttt ctgaaggacc cctacagctg gcctgcccca tgcttgatca    480
ttgcatccaa tatctttatt gtggctacat ttcagattga aagcgcctg tcagtgggtg     540 ccctgacaga gcagatgggg ctgctgctac atgtggttaa cctggccaca attatctgct   600
tcccagcagc tgtggcctta ctggttgagt ctatcactcc agtgggttcc ctgtttgctc    660
tggcatcata ctccatcatc ttcctcaagc ttttctccta ccgggatgtc aatctgtggt   720
gccgccagcg aagggtcaag gccaaagctg tgtctgcagg gaagaaggtc agtggggctg   780
ctgcccagaa cactgtaagc tatccggaca acctgaccta ccgagatctc tattacttca    840
tctttgctcc tactttgtgt tatgaactca actttcctcg atcccccga atacgaaagc    900 gctttctgct acgcgggtt cttgagatgc tcttttttcac ccagcttcaa gtggggctga    960
tccagcagtg gatggtccct actatccaga actccatgaa gcccttcaag gacatggact  1020
attcacgaat cattgagcgt tcttaaagc tggcggtccc caaccatctg atatggctca    1080
tcttcttcta ttggcttttc cactcatgtc tcaatgctgt ggcagagctc ctgcagtttg   1140
gagaccgcga gttctacagg gactggtgga atgctgagtc tgtcacctac ttttggcaga   1200
actggaatat ccccgtgcac aagtggtgca tcagacactt ctacaagcct atgctcagac   1260
tgggcagcaa caaatggatg ccaggactg ggtctttttt ggcgtcagcc ttcttccatg     1320
agtacctagt gagcattccc ctgaggatgt tccgcctctg gcattcaca gccatgatgg    1380 ctcaggtccc actggcctgg attgtgaacc gcttcttcca agggaactat ggcaatgcag   1440
ctgtgtgggt gacactcatc attgggcaac cggtggctgt gctcatgtat gtccacgact  1500
```

| | |
|---|---|
| actacgtgct caactatgat gccccagtgg gggcctgagc tactgccaaa ggccagccct | 1560 |
| ccctaacctg ggcctggagt tctggagggc ttcctggctg cctgcacact cctcctagtc | 1620 |
| tgggaggcct ctctgcccct atggggccta ctcctgctct tggggatggc acctgagtcc | 1680 |
| agctggtatg agccagtgct gggagtctgt gctgaccagg ggctgaggat atcaataaag | 1740 |
| agctatctaa aaaaaaaaaa aaaaaa | 1766 |

<210> SEQ ID NO 16
<211> LENGTH: 1766
<212> TYPE: DNA
<213> ORGANISM: Rattus sp.

<400> SEQUENCE: 16

| | |
|---|---|
| cacgactggg ccgcgacgtg gtgcgggccg aagccatggg cgaccgcgga ggcgcgggaa | 60 |
| gctctcggcg tcggaggacc ggctcgcggg tttccatcca gggtggtagt gggcccatgg | 120 |
| tagacgaaga ggaggtgcga gacgccgctg tgggccccga cttgggcgcc gggggtgacg | 180 |
| ctccggctcc ggctccggtt ccggctccag cccacacccg ggacaaagac cggcagacca | 240 |
| gcgtgggcga cggccactgg gagctgaggt gccatcgtct gcaagactct tgttcagct | 300 |
| cagacagcgg tttcagcaat taccgtggta tcctgaattg gtgcgtggtg atgctgatcc | 360 |
| tgagtaatgc aaggttattt ttagagaatc ttatcaagta tggcatcctg gtggatccca | 420 |
| tccaggtggt gtctctgttt ctgaaggacc cctacagctg gcctgcccca tgcttgatca | 480 |
| ttgcatccaa tatctttatt gtggctacat ttcagattga gaagcgcctg tcagtgggtg | 540 |
| ccctgacaga gcagatgggg ctgctgctac atgtggttaa cctggccaca attatctgct | 600 |
| tcccagcagc tgtggcctta ctggttgagt ctatcactcc agtgggttcc ctgtttgctc | 660 |
| tggcatcata ctccatcatc ttcctcaagc ttttctccta ccgggatgtc aatctgtggt | 720 |
| gccgccagcg aagggtcaag gccaaagctg tgtctgcagg gaagaaggtc agtggggctg | 780 |
| ctgcccagaa cactgtaagc tatccggaca acctgaccta ccgagatctc tattacttca | 840 |
| tctttgctcc tactttgtgt tatgaactca actttcctcg atccccccga atacgaaagc | 900 |
| gctttctgct acggcgggtt cttgagatgc tctttttcac ccagcttcaa gtggggctga | 960 |
| tccagcagtg gatggtccct actatccaga actccatgaa gcccttcaag gacatggact | 1020 |
| attcacgaat cattgagcgt ctcttaaagc tggcggtccc caaccatctg atatggctca | 1080 |
| tcttcttcta ttggcttttc cactcatgtc tcaatgctgt ggcagagctc ctgcagtttg | 1140 |
| gagaccgcga gttctacagg gactggtgga atgctgagtc tgtcacctac ttttggcaga | 1200 |
| actggaatat ccccgtgcac aagtggtgca tcagacactt ctacaagcct atgctcagac | 1260 |
| tgggcagcaa caaatggatg gccaggactg gggtcttttt ggcgtcagcc ttcttccatg | 1320 |
| agtacctagt gagcattccc ctgaggatgt tccgcctctg gcattcaca gccatgatgg | 1380 |
| ctcaggtccc actggcctgg attgtgaacc gcttcttcca agggaactat ggcaatgcag | 1440 |
| ctgtgtgggt gacactcatc attgggcaac cggtggctgt gctcatgtat gtccacgact | 1500 |
| actacgtgct caactatgat gccccagtgg gggcctgagc tactgccaaa ggccagccct | 1560 |
| ccctaacctg ggcctggagt tctggagggc ttcctggctg cctgcacact cctcctagtc | 1620 |
| tgggaggcct ctctgcccct atggggccta ctcctgctct tggggatggc acctgagtcc | 1680 |
| agctggtatg agccagtgct gggagtctgt gctgaccagg ggctgaggat atcaataaag | 1740 |
| agctatctaa aaaaaaaaaa aaaaaa | 1766 |

-continued

```
<210> SEQ ID NO 17
<211> LENGTH: 500
<212> TYPE: PRT
<213> ORGANISM: Rattus sp.

<400> SEQUENCE: 17

Met Gly Asp Arg Gly Gly Ala Gly Ser Ser Arg Arg Arg Thr Gly
 1               5                  10                  15

Ser Arg Val Ser Ile Gln Gly Gly Ser Gly Pro Met Val Asp Glu
                20                  25                  30

Glu Val Arg Asp Ala Ala Val Gly Pro Asp Leu Gly Ala Gly Asp
                35                  40                  45

Ala Pro Ala Pro Ala Pro Val Pro Ala Pro Ala His Thr Arg Asp Lys
 50                  55                  60

Asp Arg Gln Thr Ser Val Gly Asp Gly His Trp Glu Leu Arg Cys His
 65                  70                  75                  80

Arg Leu Gln Asp Ser Leu Phe Ser Ser Asp Ser Gly Phe Ser Asn Tyr
                85                  90                  95

Arg Gly Ile Leu Asn Trp Cys Val Val Met Leu Ile Leu Ser Asn Ala
                100                 105                 110

Arg Leu Phe Leu Glu Asn Leu Ile Lys Tyr Gly Ile Leu Val Asp Pro
                115                 120                 125

Ile Gln Val Val Ser Leu Phe Leu Lys Asp Pro Tyr Ser Trp Pro Ala
                130                 135                 140

Pro Cys Leu Ile Ile Ala Ser Asn Ile Phe Ile Val Ala Thr Phe Gln
145                 150                 155                 160

Ile Glu Lys Arg Leu Ser Val Gly Ala Leu Thr Glu Gln Met Gly Leu
                165                 170                 175

Leu Leu His Val Val Asn Leu Ala Thr Ile Ile Cys Phe Pro Ala Ala
                180                 185                 190

Val Ala Leu Leu Val Glu Ser Ile Thr Pro Val Gly Ser Leu Phe Ala
                195                 200                 205

Leu Ala Ser Tyr Ser Ile Ile Phe Leu Lys Leu Phe Ser Tyr Arg Asp
                210                 215                 220

Val Asn Leu Trp Cys Arg Gln Arg Arg Val Lys Ala Lys Ala Val Ser
225                 230                 235                 240

Ala Gly Lys Lys Val Ser Gly Ala Ala Ala Gln Asn Thr Val Ser Tyr
                245                 250                 255

Pro Asp Asn Leu Thr Tyr Arg Asp Leu Tyr Tyr Phe Ile Phe Ala Pro
                260                 265                 270

Thr Leu Cys Tyr Glu Leu Asn Phe Pro Arg Ser Pro Arg Ile Arg Lys
                275                 280                 285

Arg Phe Leu Leu Arg Arg Val Leu Glu Met Leu Phe Phe Thr Gln Leu
                290                 295                 300

Gln Val Gly Leu Ile Gln Gln Trp Met Val Pro Thr Ile Gln Asn Ser
305                 310                 315                 320

Met Lys Pro Phe Lys Asp Met Asp Tyr Ser Arg Ile Ile Glu Arg Leu
                325                 330                 335

Leu Lys Leu Ala Val Pro Asn His Leu Ile Trp Leu Ile Phe Phe Tyr
                340                 345                 350

Trp Leu Phe His Ser Cys Leu Asn Ala Val Ala Glu Leu Leu Gln Phe
                355                 360                 365

Gly Asp Arg Glu Phe Tyr Arg Asp Trp Trp Asn Ala Glu Ser Val Thr
                370                 375                 380
```

```
Tyr Phe Trp Gln Asn Trp Asn Ile Pro Val His Lys Trp Cys Ile Arg
385                 390                 395                 400

His Phe Tyr Lys Pro Met Leu Arg Leu Gly Ser Asn Lys Trp Met Ala
            405                 410                 415

Arg Thr Gly Val Phe Leu Ala Ser Ala Phe Phe His Glu Tyr Leu Val
        420                 425                 430

Ser Ile Pro Leu Arg Met Phe Arg Leu Trp Ala Phe Thr Ala Met Met
    435                 440                 445

Ala Gln Val Pro Leu Ala Trp Ile Val Asn Arg Phe Phe Gln Gly Asn
450                 455                 460

Tyr Gly Asn Ala Ala Val Trp Val Thr Leu Ile Ile Gly Gln Pro Val
465                 470                 475                 480

Ala Val Leu Met Tyr Val His Asp Tyr Tyr Val Leu Asn Tyr Asp Ala
                485                 490                 495

Pro Val Gly Ala
            500

<210> SEQ ID NO 18
<211> LENGTH: 496
<212> TYPE: PRT
<213> ORGANISM: Caenorhabditis elegans

<400> SEQUENCE: 18

Met Arg Gln Gln Thr Gly Arg Arg Arg Gln Pro Ser Glu Thr Ser
 1               5                  10                  15

Asn Gly Ser Leu Ala Ser Ser Arg Arg Ser Ser Phe Ala Gln Asn Gly
            20                  25                  30

Asn Ser Ser Arg Lys Ser Ser Glu Met Arg Gly Pro Cys Glu Lys Val
        35                  40                  45

Val His Thr Ala Gln Asp Ser Leu Phe Ser Thr Ser Ser Gly Trp Thr
    50                  55                  60

Asn Phe Arg Gly Phe Phe Asn Leu Ser Ile Leu Leu Val Leu Ser
65                  70                  75                  80

Asn Gly Arg Val Ala Leu Glu Asn Val Ile Lys Tyr Gly Ile Leu Ile
                85                  90                  95

Thr Pro Leu Gln Trp Ile Ser Thr Phe Val Glu His His Tyr Ser Ile
            100                 105                 110

Trp Ser Trp Pro Asn Leu Ala Leu Ile Leu Cys Ser Asn Ile Gln Ile
        115                 120                 125

Leu Ser Val Phe Gly Met Glu Lys Ile Leu Glu Arg Gly Trp Leu Gly
    130                 135                 140

Asn Gly Phe Ala Ala Val Phe Tyr Thr Ser Leu Val Ile Ala His Leu
145                 150                 155                 160

Thr Ile Pro Val Val Thr Leu Thr His Lys Trp Lys Asn Pro Leu
                165                 170                 175

Trp Ser Val Val Met Met Gly Val Tyr Val Ile Glu Ala Leu Lys Phe
            180                 185                 190

Ile Ser Tyr Gly His Val Asn Tyr Trp Ala Arg Asp Ala Arg Arg Lys
        195                 200                 205

Ile Thr Glu Leu Lys Thr Gln Val Thr Asp Leu Ala Lys Lys Thr Cys
    210                 215                 220

Asp Pro Lys Gln Phe Trp Asp Leu Lys Asp Glu Leu Ser Met His Gln
225                 230                 235                 240

Met Ala Ala Gln Tyr Pro Ala Asn Leu Thr Leu Ser Asn Ile Tyr Tyr
                245                 250                 255
```

-continued

```
Phe Met Ala Ala Pro Thr Leu Cys Tyr Glu Phe Lys Phe Pro Arg Leu
            260                 265                 270

Leu Arg Ile Arg Lys His Phe Leu Ile Lys Arg Thr Val Glu Leu Ile
        275                 280                 285

Phe Leu Ser Phe Leu Ile Ala Ala Leu Val Gln Gln Trp Val Val Pro
    290                 295                 300

Thr Val Arg Asn Ser Met Lys Pro Leu Ser Glu Met Glu Tyr Ser Arg
305                 310                 315                 320

Cys Leu Glu Arg Leu Leu Lys Leu Ala Ile Pro Asn His Leu Ile Trp
                325                 330                 335

Leu Leu Phe Phe Tyr Thr Phe Phe His Ser Phe Leu Asn Leu Ile Ala
            340                 345                 350

Glu Leu Leu Arg Phe Ala Asp Arg Glu Phe Tyr Arg Asp Phe Trp Asn
        355                 360                 365

Ala Glu Thr Ile Gly Tyr Phe Trp Lys Ser Trp Asn Ile Pro Val His
    370                 375                 380

Arg Phe Ala Val Arg His Ile Tyr Ser Pro Met Met Arg Asn Asn Phe
385                 390                 395                 400

Ser Lys Met Ser Ala Phe Phe Val Val Phe Phe Val Ser Ala Phe Phe
                405                 410                 415

His Glu Tyr Leu Val Ser Val Pro Leu Lys Ile Phe Arg Leu Trp Ser
            420                 425                 430

Tyr Tyr Gly Met Met Gly Gln Ile Pro Leu Ser Ile Ile Thr Asp Lys
        435                 440                 445

Val Val Arg Gly Gly Arg Thr Gly Asn Ile Ile Val Trp Leu Ser Leu
    450                 455                 460

Ile Val Gly Gln Pro Leu Ala Ile Leu Met Tyr Gly His Asp Trp Tyr
465                 470                 475                 480

Ile Leu Asn Phe Gly Val Ser Ala Val Gln Asn Gln Thr Val Gly Ile
                485                 490                 495
```

<210> SEQ ID NO 19
<211> LENGTH: 300
<212> TYPE: DNA
<213> ORGANISM: Caenorhabditis elegans

<400> SEQUENCE: 19

```
tttgatatgt acggtaaatg gaaaaaaggt attcatgtat ggcaaggtgg taataaatgg     60
cactaaatat gtttcaaaag tgtgagcaaa cgtatgtgag agacgagaaa aataagaaaa    120
cgacctgtaa tacatgaaaa atatcaatag gaattttgag ataatttggc aacatgcaat    180
ataatgatta taataaaaaa cttgtcttaa gactagagaa ctgctaattc aaaaaaaaca    240
aattgagata aatcaaatac caacggtttg gttttgaact gctgaaacac caaagttcaa    300
```

<210> SEQ ID NO 20
<211> LENGTH: 381
<212> TYPE: DNA
<213> ORGANISM: Caenorhabditis elegans
<220> FEATURE:
<221> NAME/KEY: misc_feature
<222> LOCATION: (46)
<223> OTHER INFORMATION: n at position 46 is unknown

<400> SEQUENCE: 20

```
tgcaaatgcg tcaacaaacg ggacgacggc ggcgtcagcc ttcggnaaac atctaatggt     60
tctttggctt ccagtagacg ctcctcattt gcacaaaatg gtaattcgtc aagggaaaag    120
```

```
ttcagaaatg agaggacctt gcgagaaagt ggtacatact gctcaagatt cattgttttc    180
gacgagttct ggatggacaa atttccgtgg attcttcaat ttgtctattt tacttttggt    240
actttcaaat ggacgcgtgg cacttgaaaa tgtgatcaaa tatggtattt tgataacacc    300
ccttcagtgg atctcaacgt tgttgagca tcactactca atttggagct ggccaaatct    360
tgctctcatc ctatgctcaa a                                              381
```

<210> SEQ ID NO 21
<211> LENGTH: 6
<212> TYPE: PRT
<213> ORGANISM: Conserved Peptide Sequence

<400> SEQUENCE: 21

```
Met Lys Ala His Ser Phe
 1               5
```

<210> SEQ ID NO 22
<211> LENGTH: 409
<212> TYPE: PRT
<213> ORGANISM: Human
<300> PUBLICATION INFORMATION:
<303> JOURNAL: J. Biol. Chem.
<304> VOLUME: 268
<306> PAGES: 20747-20755
<307> DATE: 1993

<400> SEQUENCE: 22

```
Arg Arg Ser Leu Leu Asp Glu Leu Leu Glu Val Asp His Ile Arg Thr
 1               5                  10                  15

Ile Tyr His Met Phe Ile Ala Leu Leu Ile Leu Phe Ile Leu Ser Thr
                20                  25                  30

Leu Val Val Asp Tyr Ile Asp Glu Gly Arg Leu Val Leu Glu Phe Ser
            35                  40                  45

Leu Leu Ser Tyr Ala Phe Gly Lys Phe Pro Thr Val Val Trp Thr Trp
        50                  55                  60

Trp Ile Met Phe Leu Ser Thr Phe Ser Val Pro Tyr Phe Leu Phe Gln
 65                  70                  75                  80

His Trp Arg Thr Gly Tyr Ser Lys Ser His Pro Leu Ile Arg Ser
                85                  90                  95

Leu Phe His Gly Phe Leu Phe Met Ile Phe Gln Ile Gly Val Leu Gly
                100                 105                 110

Phe Gly Pro Thr Tyr Val Val Leu Ala Tyr Thr Leu Pro Pro Ala Ser
            115                 120                 125

Arg Phe Ile Ile Ile Phe Glu Gln Ile Arg Phe Val Met Lys Ala His
        130                 135                 140

Ser Phe Val Arg Glu Asn Val Pro Arg Val Leu Asn Ser Ala Lys Glu
145                 150                 155                 160

Lys Ser Ser Thr Val Pro Ile Pro Thr Val Asn Gln Tyr Leu Tyr Phe
                165                 170                 175

Leu Phe Ala Pro Thr Leu Ile Tyr Arg Asp Ser Tyr Pro Arg Asn Pro
            180                 185                 190

Thr Val Arg Trp Gly Tyr Val Ala Met Lys Phe Ala Gln Val Phe Gly
        195                 200                 205

Cys Phe Phe Tyr Val Tyr Tyr Ile Phe Glu Arg Leu Cys Ala Pro Leu
        210                 215                 220

Phe Arg Asn Ile Lys Gln Glu Pro Phe Ser Ala Arg Val Leu Val Leu
225                 230                 235                 240
```

```
Cys Val Phe Asn Ser Ile Leu Pro Gly Val Leu Ile Leu Phe Leu Thr
            245                 250                 255

Phe Phe Ala Phe Leu His Cys Trp Leu Asn Ala Phe Ala Glu Met Leu
        260                 265                 270

Arg Phe Gly Asp Arg Met Phe Tyr Lys Asp Trp Trp Asn Ser Thr Ser
            275                 280                 285

Tyr Ser Asn Tyr Tyr Arg Thr Trp Asn Val Val His Asp Trp Leu
290                 295                 300

Tyr Tyr Tyr Ala Tyr Lys Asp Phe Leu Trp Phe Phe Ser Lys Arg Phe
305                 310                 315                 320

Lys Ser Ala Ala Met Leu Ala Val Phe Ala Val Ser Ala Val Val His
                325                 330                 335

Glu Tyr Ala Leu Ala Val Cys Leu Ser Phe Phe Tyr Pro Val Leu Phe
            340                 345                 350

Val Leu Phe Met Phe Phe Gly Met Ala Phe Asn Phe Ile Val Asn Asp
        355                 360                 365

Ser Arg Lys Lys Pro Ile Trp Asn Val Leu Met Trp Thr Ser Leu Phe
    370                 375                 380

Leu Gly Asn Gly Val Leu Leu Cys Phe Tyr Ser Gln Glu Trp Tyr Ala
385                 390                 395                 400

Arg Arg His Cys Pro Leu Lys Asn Pro
            405
```

<210> SEQ ID NO 23
<211> LENGTH: 409
<212> TYPE: PRT
<213> ORGANISM: murine
<300> PUBLICATION INFORMATION:
<303> JOURNAL: J. Biol. Chem.
<304> VOLUME: 270
<306> PAGES: 26192-26201
<307> DATE: 1995

<400> SEQUENCE: 23

```
Arg Gln Ser Leu Leu Asp Glu Leu Phe Glu Val Asp His Ile Arg Thr
1               5                   10                  15

Ile Tyr His Met Phe Ile Ala Leu Leu Ile Leu Phe Val Leu Ser Thr
                20                  25                  30

Ile Val Val Asp Tyr Ile Asp Glu Gly Arg Leu Val Leu Glu Phe Asn
            35                  40                  45

Leu Leu Ala Tyr Ala Phe Gly Lys Phe Pro Thr Val Ile Trp Thr Trp
        50                  55                  60

Trp Ala Met Phe Leu Ser Thr Leu Ser Ile Pro Tyr Phe Leu Phe Gln
65                  70                  75                  80

Pro Trp Ala His Gly Tyr Ser Lys Ser Ser His Pro Leu Ile Tyr Ser
                85                  90                  95

Leu Val His Gly Leu Leu Phe Leu Val Phe Gln Leu Gly Val Leu Gly
            100                 105                 110

Phe Val Pro Thr Tyr Val Val Leu Ala Tyr Thr Leu Pro Pro Ala Ser
        115                 120                 125

Arg Phe Ile Leu Ile Leu Glu Gln Ile Arg Leu Ile Met Lys Ala His
    130                 135                 140

Ser Phe Val Arg Glu Asn Ile Pro Arg Val Leu Asn Ala Ala Lys Glu
145                 150                 155                 160

Lys Ser Ser Lys Asp Pro Leu Pro Thr Val Asn Gln Tyr Leu Tyr Phe
                165                 170                 175
```

-continued

```
Leu Phe Ala Pro Thr Leu Ile Tyr Arg Asp Asn Tyr Pro Arg Thr Pro
                180                 185                 190

Thr Val Arg Trp Gly Tyr Val Ala Met Gln Phe Leu Gln Val Phe Gly
            195                 200                 205

Cys Leu Phe Tyr Val Tyr Ile Phe Glu Arg Leu Cys Ala Pro Leu
        210                 215                 220

Phe Arg Asn Ile Lys Gln Glu Pro Phe Ser Ala Arg Val Leu Val Leu
225                 230                 235                 240

Cys Val Phe Asn Ser Ile Leu Pro Gly Val Leu Ile Leu Phe Leu Ser
                245                 250                 255

Phe Phe Ala Phe Leu His Cys Trp Leu Asn Ala Phe Ala Glu Met Leu
                260                 265                 270

Arg Phe Gly Asp Arg Met Phe Tyr Lys Asp Trp Trp Asn Ser Thr Ser
                275                 280                 285

Tyr Ser Asn Tyr Tyr Arg Thr Trp Asn Val Val His Asp Trp Leu
        290                 295                 300

Tyr Tyr Tyr Val Tyr Lys Asp Leu Leu Trp Phe Ser Lys Arg Phe
305                 310                 315                 320

Lys Ser Ala Ala Met Leu Ala Val Phe Ala Leu Ser Ala Val Val His
                325                 330                 335

Glu Tyr Ala Leu Ala Ile Cys Leu Ser Tyr Phe Tyr Pro Val Leu Phe
                340                 345                 350

Val Leu Phe Met Phe Phe Gly Met Ala Phe Asn Phe Ile Val Asn Asp
                355                 360                 365

Ser Arg Lys Arg Pro Ile Trp Asn Ile Met Val Trp Ala Ser Leu Phe
        370                 375                 380

Leu Gly Tyr Gly Leu Ile Leu Cys Phe Tyr Ser Gln Glu Trp Tyr Ala
385                 390                 395                 400

Arg Gln His Cys Pro Leu Lys Asn Pro
                405
```

<210> SEQ ID NO 24
<211> LENGTH: 429
<212> TYPE: PRT
<213> ORGANISM: yeast
<300> PUBLICATION INFORMATION:
<303> JOURNAL: J. Biol. Chem.
<304> VOLUME: 271
<306> PAGES: 24157-24163
<307> DATE: 1996

<400> SEQUENCE: 24

```
Asp Lys Ala Asp Ala Pro Pro Gly Glu Lys Leu Glu Ser Asn Phe Ser
1               5                   10                  15

Gly Ile Tyr Val Phe Ala Trp Met Phe Leu Gly Trp Ile Ala Ile Arg
                20                  25                  30

Cys Cys Thr Asp Tyr Tyr Ala Ser Tyr Gly Ser Ala Trp Asn Lys Leu
            35                  40                  45

Glu Ile Val Gln Tyr Met Thr Thr Asp Leu Phe Thr Ile Ala Met Leu
        50                  55                  60

Asp Leu Ala Met Phe Leu Cys Thr Phe Val Val Phe Val His Trp
65                  70                  75                  80

Leu Val Lys Lys Arg Ile Ile Asn Trp Lys Trp Thr Gly Phe Val Ala
                85                  90                  95

Val Ser Ile Phe Glu Leu Ala Phe Ile Pro Val Thr Phe Pro Ile Tyr
                100                 105                 110
```

```
Val Tyr Tyr Phe Asp Phe Asn Trp Val Thr Arg Ile Phe Leu Phe Leu
        115                 120                 125

His Ser Val Val Phe Val Met Lys Ser His Ser Phe Ala Phe Tyr Asn
    130                 135                 140

Gly Tyr Leu Trp Asp Ile Lys Gln Glu Leu Glu Tyr Ser Ser Lys Gln
145                 150                 155                 160

Leu Gln Lys Tyr Lys Glu Ser Leu Ser Pro Glu Thr Arg Glu Ile Leu
                165                 170                 175

Gln Lys Ser Cys Asp Phe Cys Leu Phe Glu Leu Asn Tyr Gln Thr Lys
                180                 185                 190

Asp Asn Asp Phe Pro Asn Asn Ile Ser Cys Ser Asn Phe Phe Met Phe
            195                 200                 205

Cys Leu Phe Pro Val Leu Val Tyr Gln Ile Asn Tyr Pro Arg Thr Ser
        210                 215                 220

Arg Ile Arg Trp Arg Tyr Val Leu Glu Lys Val Cys Ala Ile Ile Gly
225                 230                 235                 240

Thr Ile Phe Leu Met Met Val Thr Ala Gln Phe Phe Met His Pro Val
                245                 250                 255

Ala Met Arg Cys Ile Gln Phe His Asn Thr Pro Thr Phe Gly Gly Trp
            260                 265                 270

Ile Pro Ala Thr Gln Glu Trp Phe His Leu Leu Phe Asp Met Ile Pro
        275                 280                 285

Gly Phe Thr Val Leu Tyr Met Leu Thr Phe Tyr Met Ile Trp Asp Ala
    290                 295                 300

Leu Leu Asn Cys Val Ala Glu Leu Thr Arg Phe Ala Asp Arg Tyr Phe
305                 310                 315                 320

Tyr Gly Asp Trp Trp Asn Cys Val Ser Phe Glu Glu Phe Ser Arg Ile
                325                 330                 335

Trp Asn Val Pro Val His Lys Phe Leu Leu Arg His Val Tyr His Ser
            340                 345                 350

Ser Met Gly Ala Leu His Leu Ser Lys Ser Gln Ala Thr Leu Phe Thr
        355                 360                 365

Phe Phe Leu Ser Ala Val His Glu Met Ala Met Phe Ala Ile Phe
    370                 375                 380

Arg Arg Val Arg Gly Tyr Leu Phe Met Phe Gln Leu Ser Gln Phe Val
385                 390                 395                 400

Trp Thr Ala Leu Ser Asn Thr Lys Phe Leu Arg Ala Arg Pro Gln Leu
                405                 410                 415

Ser Asn Val Val Phe Ser Phe Gly Val Cys Ser Gly Pro
            420                 425

<210> SEQ ID NO 25
<211> LENGTH: 432
<212> TYPE: PRT
<213> ORGANISM: yeast
<300> PUBLICATION INFORMATION:
<303> JOURNAL: Science
<304> VOLUME: 272
<306> PAGES: 1353-1356
<307> DATE: 1996

<400> SEQUENCE: 25

Glu Thr Val Val Thr Val Glu Thr Thr Ile Ile Ser Ser Asn Phe Ser
1               5                   10                  15

Gly Leu Tyr Val Ala Phe Trp Met Ala Ile Ala Phe Gly Ala Val Lys
            20                  25                  30
```

```
Ala Leu Ile Asp Tyr Tyr Gln His Asn Gly Ser Phe Lys Asp Ser
         35                  40                  45

Glu Ile Leu Lys Phe Met Thr Thr Asn Leu Phe Thr Val Ala Ser Val
 50                  55                  60

Asp Leu Leu Met Tyr Leu Ser Thr Tyr Phe Val Val Gly Ile Gln Tyr
 65                  70                  75                  80

Leu Cys Lys Trp Gly Val Leu Lys Trp Gly Thr Thr Gly Trp Ile Phe
                 85                  90                  95

Thr Ser Ile Tyr Glu Phe Leu Phe Val Ile Phe Tyr Met Tyr Leu Thr
                100                 105                 110

Glu Asn Ile Leu Lys Leu His Trp Leu Ser Lys Ile Phe Leu Phe Leu
                115                 120                 125

His Ser Leu Val Leu Leu Met Lys Met His Ser Phe Ala Phe Tyr Asn
        130                 135                 140

Gly Tyr Leu Trp Gly Ile Lys Glu Glu Leu Gln Phe Ser Lys Ser Ala
145                 150                 155                 160

Leu Ala Lys Tyr Lys Asp Ser Ile Asn Asp Pro Lys Val Ile Gly Ala
                165                 170                 175

Leu Glu Lys Ser Cys Glu Phe Cys Ser Phe Glu Leu Ser Ser Gln Ser
                180                 185                 190

Leu Ser Asp Gln Thr Gln Lys Phe Pro Asn Asn Ile Ser Ala Lys Ser
        195                 200                 205

Phe Phe Trp Phe Thr Met Phe Pro Thr Leu Ile Tyr Gln Ile Glu Tyr
        210                 215                 220

Pro Arg Thr Lys Glu Ile Arg Trp Ser Tyr Val Leu Glu Lys Ile Cys
225                 230                 235                 240

Ala Ile Phe Gly Thr Ile Phe Leu Met Met Ile Asp Ala Gln Ile Leu
                245                 250                 255

Met Tyr Pro Val Ala Met Arg Ala Leu Ala Val Arg Asn Ser Glu Trp
                260                 265                 270

Thr Gly Ile Leu Asp Arg Leu Leu Lys Trp Val Gly Leu Leu Val Asp
        275                 280                 285

Ile Val Pro Gly Phe Ile Val Met Tyr Ile Leu Asp Phe Tyr Leu Ile
        290                 295                 300

Trp Asp Ala Ile Leu Asn Cys Val Ala Glu Leu Thr Arg Phe Gly Asp
305                 310                 315                 320

Arg Tyr Phe Tyr Gly Asp Trp Trp Asn Cys Val Ser Trp Ala Asp Phe
                325                 330                 335

Ser Arg Ile Trp Asn Ile Pro Val His Lys Phe Leu Leu Arg His Val
                340                 345                 350

Tyr His Ser Ser Met Ser Ser Phe Lys Leu Asn Lys Ser Gln Ala Thr
        355                 360                 365

Leu Met Thr Phe Phe Leu Ser Ser Val Val His Glu Leu Ala Met Tyr
        370                 375                 380

Val Ile Phe Lys Lys Leu Arg Phe Tyr Leu Phe Phe Gln Met Leu
385                 390                 395                 400

Gln Met Pro Leu Val Ala Leu Thr Asn Thr Lys Phe Met Arg Asn Arg
                405                 410                 415

Thr Ile Ile Gly Asn Val Ile Phe Trp Leu Gly Ile Cys Met Gly Pro
                420                 425                 430
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Arabidopsis
      ACAT-Like primer for 5' RACE

<400> SEQUENCE: 26
tgcaaattga cgagcacacc aaccccttc                               29

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Arabidopsis
      ACAT-Like primer for 5' RACE

<400> SEQUENCE: 27
aaggatgctt tgagttcctg acaatagg                                28

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:Rat 5' PCR
      primer

<400> SEQUENCE: 28
taggtgacag actcagcatt ccaccagtcc c                            31

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Rat ACAT-like
      nested PCR primer

<400> SEQUENCE: 29
cgccagcttt aagagacgct caatgattcg                              30

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Rat ACAT-like
      PCR primer

<400> SEQUENCE: 30
ggatccctgc aggtcaggcc cccactgggg catcata                      37

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Rat ACAT-like
      PCR primer-3'

<400> SEQUENCE: 31
ggatccgcgg ccgcacaatg ggcgaccgcg gaggcgcggg a                 41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:C. elegans
      ACAT-like PCR primer-5'

<400> SEQUENCE: 32
ggatccgcgg ccgcacaatg cgtcaacaaa cgggacgacg g                         41

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: C. elegans
      ACAT-like PCR primer-3'

<400> SEQUENCE: 33
ggatcccctg caggtcaaat accaacggtt tggttttg                             38

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Arabidopsis 5'
      PCR primer

<400> SEQUENCE: 34
tcgacctgca ggaagcttag aaatggcgat tttggattc                            39

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Arabidopsis
      ACAT-like 3' PCR primer

<400> SEQUENCE: 35
ggatccgcgg ccgctcatga catcgatcct tttcgg                               36

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 36
cgcgatttaa atggcgcgcc ctgcaggcgg ccgcctgcag ggcgcgccat ttaa           54

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: pCGN8618
      Cloning Oligonucleotide

<400> SEQUENCE: 37
tcgaggatcc gcggccgcaa gcttcctgca gg                                   32

```
<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: pCGN8618
      Cloning Oligonucleotide

<400> SEQUENCE: 38
tcgacctgca ggaagcttgc ggccgcggat cc                                    32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: pCGN8619
      Cloning Oligonucleotide

<400> SEQUENCE: 39
tcgacctgca ggaagcttgc ggccgcggat cc                                    32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: pCGN8619
      Cloning Oligonucleotide

<400> SEQUENCE: 40
tcgaggatcc gcggccgcaa gcttcctgca gg                                    32

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: pCGN8620
      Cloning Oligonucleotide

<400> SEQUENCE: 41
tcgaggatcc gcggccgcaa gcttcctgca ggagct                                36

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: pCGN8620
      Cloning Oligonucleotide

<400> SEQUENCE: 42
cctgcaggaa gcttgcggcc gcggatcc                                         28

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: pCGN8621
      Cloning Oligonucleotide

<400> SEQUENCE: 43
tcgacctgca ggaagcttgc ggccgcggat ccagct                                36
```

```
<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: pCGN8621
      Cloning Oligonucleotide

<400> SEQUENCE: 44
ggatccgcgg ccgcaagctt cctgcagg                                              28

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 45
caggaggcgg ccgcaggagg ctgcaggtac                                            30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 46
cctgcagcct cctgcggccg cctcctgagc t                                          31
```

ACYL COA:CHOLESTEROL ACYLTRANSFERASE RELATED NUCLEIC ACID SEQUENCES

CROSS-REFERENCE TO RELATED APPLICATIONS

This application is a continuation of U.S. application Ser. No. 09/326,203, filed Jun. 4, 1999, now U.S. Pat. No. 6,444,876, which claims the benefit under 35 U.S.C. § 119(e) of U.S. Provisional Application Ser. No. 60/088,143, filed Jun. 5, 1998, and U.S. Provisional Application Ser. No. 60/108,389, filed Nov. 12, 1998, all of which applications are herein incorporated in their entireties by reference.

A paper copy of the Sequence Listing and a computer readable form (CRF) of the sequence listing on diskette, containing the file named 16516158(corrected).txt, which is 53,248 bytes in size (measured in MS-DOS), and which was recorded on May 13, 2004, are herein incorporated by reference.

TECHNICAL FIELD

The present invention is directed to nucleic acid and amino acid sequences and constructs, and methods related thereto.

BACKGROUND

Through the development of plant genetic engineering techniques, it is now possible to produce a transgenic variety of plant species to provide plants which have novel and desirable characteristics. For example, it is now possible to genetically engineer plants for tolerance to environmental stresses, such as resistance to pathogens and tolerance to herbicides and to improve the quality characteristics of the plant, for example improved fatty acid compositions. However, the number of useful nucleotide sequences for the engineering of such characteristics is thus far limited and the speed with which new useful nucleotide sequences for engineering new characteristics is slow.

There is a need for improved means to obtain or manipulate compositions of sterols and fatty acids from biosynthetic or natural plant sources. For example, novel oil products, improved sources of synthetic triacylglycerols (triglycerides), alternative sources of commercial oils, such as tropical oils (i.e., palm kernel and coconut oils), and plant oils found in trace amounts from natural sources are desired for a variety of industrial and food uses. Or, the ability to increase sterol production in plants may provide for novel sources of sterols for use in human and animal nutrition.

To this end, the triacylglycerol (TAG) biosynthesis system and sterol biosynthesis in mammalian tissues, yeast and plants has been studied.

Sterol biosynthesis branches from the farnesyl diphosphate intermediate in the isoprenoid pathway. Sterol biosynthesis occurs via a mevalonate dependent pathway in mammals and higher plants (Goodwin,(1981) *Biosynthesis of Isoprenoid Compounds*, vol 1 (Porter, J. W. & Spurgeon, S. L., eds) pp.443–480, John Wiley and Sons, New York), while in green algae sterol biosynthesis is thought to occur via a mevalonate independent pathway (Schwender, et al. (1997) *Physiology, Biochemistry, and Molecular Biology of Plant Lipids*, (Williams, J. P., Khan, M. U., and Lem, N. W., eds) pp. 180–182, Kluwer Academic Publishers, Norwell, Mass.).

The solubility characteristics of steroyl esters suggests that this is the storage form of sterols (Chang, et al., (1997) *Annu. Rev. Biochem.*, 66:613–638). Sterol O-acyltransferase enzymes such as acyl CoA:cholesterol acyltransferase (ACAT) catalyze the formation of cholesterol esters, and thus are key to controlling the intracellular cholesterol storage.

Such ACATs have been the subject of many research efforts, particularly for applications involving the reduction of cellular cholesterol storage in humans. Several studies suggest that cholesterol esters contribute significantly to the early formation of foam cells in atherosclerosis in humans (Fowler, et al. (1979) *Lab. Invest.* 41:372–378; Schaffner et al. (1980) *Am. J. Pathol.* 100:57–80; Lupu, et al. (1987) *Arterosclerosis* 67:127–142; Brown et al. (1983) *Annu. Rev. Biochem.* 52:223–261; the entirety of which are incorporated herein by reference)and by blocking ACAT, intracellular cholesterol esters are significantly reduced (Ross, et al. (1986) *J. Biol. Chem.* 259:815–819; Tabas, et al. (1986) *J. Biol. Chem.* 261:3147–3155; Cadigan, et al. (1988) *J. Lipid Res.* 29:1683–1692; Bocan et al. (1991) *Arterioscler. Thromb.* 11:1830–1843, the entirety of which are incorporated herein by reference). Thus, directly inhibiting ACAT within the arterial wall may inhibit the progression of atherosclerotic lesions without lowering total plasma cholesterol.

TAG biosynthesis occurs in the cytoplasmic membranes of plant seed tissues which accumulate storage triglycerides ("oil"), fatty acyl groups are added sequentially by specific acyltransferase enzymes to the sn-1, sn-2 and sn-3 positions of glycerol-3-phosphate (G3P) to form TAG. This pathway is commonly referred to as the Kennedy or G3P pathway.

The first step in TAG formation is the acylation of the sn-1 position of glycerol-3-phosphate, catalyzed by glycerophosphate acyltransferase, to form lysophosphatidic acid. The lysophosphatidic acid is subsequently acylated at the sn-2 position by lysophosphatidic acid acyltransferase (LPAAT) to create phosphatidic acid. The phosphatidic acid is subsequently dephosphorylated at the sn-3 position by phosphatidic acid phosphatase to form sn-1,2-diacylglycerol (DAG).

An important step in the formation of TAG is the acylation of the sn-3 position of sn-1,2-diacylglycerol by diacylglycerol acyltransferase (DAGAT, EC 2.3.1.20) ultimately forming triacylglycerol (TAG).

The characterization of diacylglycerol acyltransferase (also known as DAGAT) and acyl CoA:cholesterol acyltransferase (also known as ACAT) is useful for the further study of plant fatty acid and sterol synthesis systems and for the development of novel and/or alternative sterol and oils sources. Furthermore, identification of novel ACAT sequences may provide a novel means to inhibit intracellular cholesterol ester formation in animals, thus reducing atherosclerosis. Studies of plant mechanisms may provide means to further enhance, control, modify, or otherwise alter the total fatty acyl composition of triglycerides and oils. Furthermore, the elucidation of the factor(s) critical to the natural production of triglycerides in plants is desired, including the purification of such factors and the characterization of element(s) and/or cofactors which enhance the efficiency of the system. Of particular interest are the nucleic acid sequences of genes encoding proteins which may be useful for applications in genetic engineering.

SUMMARY OF THE INVENTION

The present invention is directed to acyl-CoA:cholesterol acyltansferase (EC 2.3.1.26, also referred to herein as ACAT) related polynucleotides, and in particular to ACAT-related polynucleotides. The polynucleotides of the present invention include those derived from plant, fungal, mammalian and nematode sources.

Thus, one aspect of the present invention relates to isolated polynucleotide sequences encoding ACAT related proteins. In particular, isolated nucleic acid sequences encoding ACAT related proteins from human, rat, *C. elegans*, *Arabidopsis*, soybean and corn are provided.

Another aspect of the present invention relates to oligonucleotides which include partial or complete ACAT encoding sequences.

It is also an aspect of the present invention to provide recombinant DNA constructs which can be used for transcription or transcription and translation (expression) of ACAT. In particular, constructs are provided which are capable of transcription or transcription and translation in host cells.

In another aspect of the present invention, methods are provided for production of ACAT in a host cell or progeny thereof. In particular, host cells are transformed or transfected with a DNA construct which can be used for transcription or transcription and translation of ACAT. The recombinant cells which contain ACAT are also part of the present invention.

In a further aspect, the present invention relates to methods of using polynucleotide and polypeptide sequences to modify the sterol, sterol ester, and fatty acid content as well as composition, particularly in seed tissue of oilseed crops. Plant cells having such a modified sterol and fatty acid content are also contemplated herein.

In yet a further aspect, the present invention relates to methods of using polynucleotide and polypeptide sequences to inhibit or delay the germination of seeds.

The modified plants, seeds and oils obtained by the expression of the ACAT-like proteins are also considered part of the invention.

BRIEF DESCRIPTION OF THE DRAWINGS

FIG. 1 is the encoding sequence to the *Arabidopsis thaliana* ACAT-like protein (SEQ ID NO: 1 and SEQ ID NO: 2).

FIG. 2 are soy ESTs related to the class of ACAT-like proteins (SEQ ID NOs:3–6).

FIG. 3 are maize ESTs related to the class of ACAT-like proteins (SEQ ID NOs:7–10).

FIG. 4 is a *Mortierella* ESTs related to the class of ACAT-like proteins (SEQ ID NO:11).

FIG. 5 is an encoding sequence to a mouse protein related to the class of ACAT-like proteins (SEQ ID NO:12).

FIG. 6 is another encoding sequence to a mouse protein related to the class of ACAT-like proteins (SEQ ID NO:13).

FIG. 7 is an encoding sequence to a human protein related to the class of ACAT-like proteins (SEQ ID NO:14).

FIG. 8 is an encoding sequence to a rat protein related to the class of ACAT-like proteins obtained by assemblage of single pass 5' terminal sequences of different cDNAs (SEQ ID NO:15).

FIG. 9 is a sequence comparison of various ACAT related amino acid sequences.

FIG. 10 provides the coding sequence of the Rat ACAT-like nucleic acid sequence derived from a single full length cDNA clone (SEQ ID NO:16).

FIG. 11 provides the amino acid sequence coded by the Rat ACAT-like DNA sequence of FIG. 10 (SEQ ID NO:17).

FIG. 12 provides the amino acid sequence of the ACAT-like protein obtained from *Caenorhabditis elegans* (SEQ ID NO:18).

FIG. 13 provides a partial nucleic acid sequence of the *C. elegans* ACAT-like protein (SEQ ID NO:19).

FIG. 14 provides a different partial nucleic acid sequence for the *C. elegans* ACAT-like protein (SEQ ID NO:20).

DETAILED DESCRIPTION OF THE INVENTION

Figure 9A:
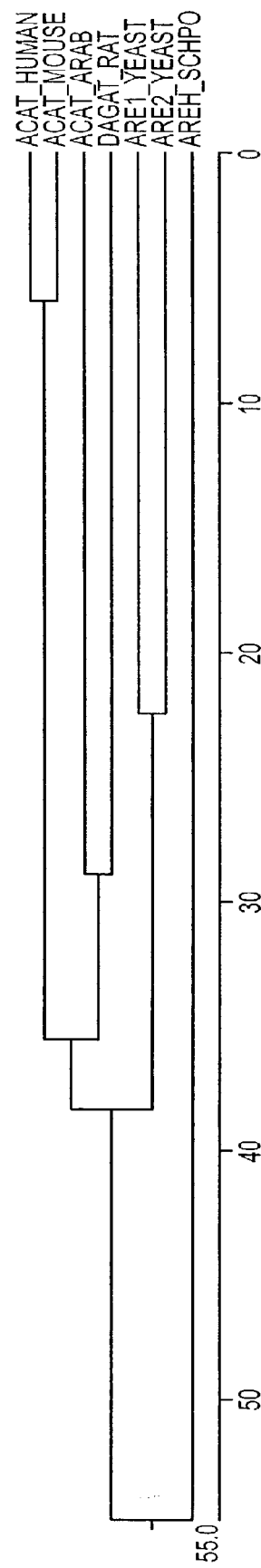
FIG. 9A shows a phylogenetic tree showing the relationship between the ACAT protein sequences.

The present invention relates to acyl CoA: cholesterol acyltransferase (hereinafter referred to as ACAT) related sequences, particularly the isolated ACAT nucleic acid sequences encoding the ACAT protein from host cell sources. A acyl CoA: cholesterol acyltransferase related sequences of this invention includes any nucleic acid sequence encoding amino acids from a source, such as a protein, polypeptide or peptide, obtainable from a cell source, which demonstrate the ability to form sterol esters from sterol and fatty acid substrates. By "enzyme reactive conditions" is meant that any necessary conditions are available in an environment (i.e., such factors as temperature, pH, lack of inhibiting substances) which will permit the enzyme to function.

Isolated Polynucleotides, Proteins, and Polypeptides

A first aspect of the present invention relates to isolated ACAT polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

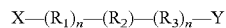

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 1 and 16. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or MRNA to identify members of the library which hybridize to the probe. For example, synthetic oligonucleotides are prepared which correspond to the ACAT EST sequences. The oligonucleotides are used as primers in polymerase chain reaction (PCR) techniques to obtain 5' and 3' terminal sequence of ACAT genes. Alternatively, where oligonucleotides of low degeneracy can be prepared from particular ACAT peptides, such probes may be used directly to screen gene libraries for ACAT gene sequences. In particular, screening of cDNA libraries in phage vectors is useful in such methods due to lower levels of background hybridization.

Typically, a ACAT sequence obtainable from the use of nucleic acid probes will show 60–70% sequence identity between the target ACAT sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an ACAT enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related ACAT genes. Shorter probes are often particularly useful for polymerase chain reactions (PCR), especially when highly conserved sequences can be identified. (See, Gould, et al., *PNAS USA* (1989) 86:1934–1938.).

Another aspect of the present invention relates to ACAT polypeptides. Such polypeptides include isolated polypeptides set forth in the Sequence Listing, as well as polypeptides and fragments thereof, particularly those polypeptides which exhibit ACAT activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine identity.

Parameters for polypeptide sequence comparison typically include the following:

Algorithm: Needleman and Wunsch, *J. Mol. Biol.* 48:443–453 (1970)

Comparison matrix: BLOSSUM62 from Hentikoff and Henlikoff, *Proc. Natl. Acad. Sci USA* 89:10915–10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443–453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

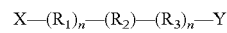

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably SEQ ID NOs: 2 and 17. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Plant Constructs and Methods of Use

Of particular interest is the use of the nucleotide sequences in recombinant DNA constructs to direct the transcription or transcription and translation (expression) of the acyltransferase sequences of the present invention in a host plant cell. The expression constructs generally comprise a promoter functional in a host plant cell operably linked to a nucleic acid sequence encoding a acyl-CoA:cholesterol acyltransferase of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378, 619). In addition, it may also be preferred to bring about expression of the acyltransferase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.,* 83:8560–8564 (1986))) and oleosin.

It may be advantageous to direct the localization of proteins conferring ACAT to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481.

Depending upon the intended use, the constructs may contain the nucleic acid sequence which encodes the entire ACAT protein, or a portion thereof. For example, where antisense inhibition of a given ACAT protein is desired, the entire ACAT sequence is not required. Furthermore, where ACAT sequences used in constructs are intended for use as probes, it may be advantageous to prepare constructs containing only a particular portion of a ACAT encoding sequence, for example a sequence which is discovered to encode a highly conserved ACAT region.

The skilled artisan will recognize that there are various methods for the inhibition of expression of endogenous sequences in a host cell. Such methods include, but are not limited to, antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the ACAT or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the ACAT sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a ACAT nucleic acid sequence.

Plant expression or transcription constructs having a plant ACAT as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of plant ACAT constructs in plants to produce plants or plant parts, including, but not limited to leaves, stems, roots, reproductive, and seed, with a modified content of lipid and/or sterol esters.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as acyltransferase enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for acyltransferase activity. Such expression systems are known in the art and are readily available through commercial sources.

Also of interest in the present invention is the use of such acyl CoA:cholesterol acyltransferase encoding nucleic acid sequences for the preparation of expression constructs to increase the production of triacylglycerol in plant. Such ACAT nucleic acid sequences may also encode sequences of amino acids, such as, a protein, polypeptide, or peptide, which demonstrates the ability to acylate the sn-3 position of sn-1,2-diacylglycerol under plant enzyme conditions. Such DAGAT sequences will find use in a variety of applications related to production of TAG in host cells. As DAGAT directed lipid synthesis towards TAG production and away from membrane lipid production, a number of uses for increasing TAG production in cells normally capable of producing TAG or providing TAG production in cells not normally capable of making TAG are considered.

For example, expression of a laurate-specific DAGAT may be used to provide for increased production of laurate (12:0) fatty acids in TAG in plant cells transformed to express a thioesterase specific for laurate production. Such plants are described, for example, in U.S. Pat. No. 5,298, 421. Plant sources for such laurate preferring DAGATs may include California bay, *Cuphea* species, and coconut.

Similarly, for increased production of stearate (18:0) fatty acids in plant seed oils, a DAGAT having preferential activity on stearate-containing DAG may be found, for example, in various tropical plant species such as *Garcinia* species, including mangosteen and kokum, plants of the *Mangifera* family, such as mango, and various other tropical plants including *Butyrospennum* (shea), *Pentadesma* (tallow tree), *Illipe* (illipe butter), *Theobroma* (cocoa), *Simarouba* (tree of paradise) and *Shorea* (sal).

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of ACAT can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as *Synechocystis, Shewanella*, yeast, *Pseudomonas, Rhodobacteria*, etc., that lack specific biochemical reactions, or that have been mutated. The sequences of the DNA coding regions can be optimized by gene resynthesis, based on codon usage, for maximum expression in particular hosts.

For the alteration of sterol and sterol ester production in a host cell, a second expression construct can be used in accordance with the present invention. For example, the ACAT expression construct can be introduced into a host cell in conjunction with a second expression construct having a nucleotide sequence for a protein involved in sterol biosynthesis.

In order to increase triglyceride (Also referred to herein as TAG) biosynthesis, and thereby increasing fatty acids, in a plant tissue, coexpression of a plant or other ACAT in a plant tissue with a second gene involved in fatty acid biosynthesis may also find use in the present invention. For example, coexpression of a ACAT sequence in plant seed tissue with a DNA sequence encoding for another protein involved in TAG biosynthesis, such as LPAAT (U.S. patent application Ser. No. 07/458,109, the entirety of which is incorporated herein by reference) may increase the flux through the kennedy pathway and increase the total fatty acids produced in the seed tissue.

Furthermore, for increased production of a particular chain length fatty acid, for example medium-chain fatty acids, coexpression of a plant or other ACAT in a plant tissue with a second DNA sequence encoding for enzymes involved in the production of medium-chain, or other chain length, fatty acids may find use in the present invention. DNA sequences encoding for thioesterases (for example U.S. Pat. Nos. 5,298,421, 5,667,997 the entirety of which are incorporated herein by reference) or fatty acid synthases (U.S. patent application Ser. No. 08/827,828 the entirety of which is incorporated herein by reference) are examples of enzymes involved in the production of various chain length fatty acids.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permiissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region (s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the ACAT expression construct, or alternatively, transformed plants, one expressing the ACAT construct and one expressing the second construct, can be crossed to bring the constructs together in the same plant.

The invention also relates to vectors that include a polynucleotide or polynucleotides of the invention, host cells that are genetically engineered with vectors of the invention and the production of polypeptides of the invention by recombinant techniques. Cell free translation systems can be employed to produce such protein using RNAs derived from the DNA constructs of the invention.

For recombinant production, host cells can be genetically engineered to incorporate expression systems or portions thereof or polynucleotides of the present invention. Introduction of a polynucleotide into a host cell can be effected by methods described in many standard laboratory manuals, such as Davis et al., Basic Methods in Molecular Biology, (1986) and Sambrook et al, Molecular Cloning: A Laboratory Manual, $2^{nd}$ Edition, Cold Spring Harbor Laboratory Press, Cold Spring Harbor N.Y. (1989). Such methods include, but are not limited to, calcium phosphate transfection, DEAE dextran mediated transfection, transvection, microinjection, cationic lipid-mediated transfection, electroporation, transduction, scrape loading ballistic introduction and infection.

Representative examples of appropriate hosts include bacterial cells, such as streptococci, staphylococci, enterococci, *E. coli*, streptomyces, and *Bacillus subtilis* cells; fungal cells, such as yeast cells and *Aspergillus* cells; insect cells, such as *Drosophila* S2 and *Spodoptera* Sf9 cells; animal cells such as CHO, COS, HeLa, C127, 3T3, BHK, 293 and Bowes melanoma cells; and plant cells as described above.

A variety of expression systems can be used to produce the polypeptides, of the invention. Such vectors include, but are not limited to, chromosomal, episomal, and virus derived vectors, for example vectors from bacterial plasmids, bacteriophage, transposons, yeast episomes, insertion elements, yeast chromosomal elements, viruses such as baculoviruses, papova viruses, such as SB40, vaccinia viruses, adenoviruses, fowl pox viruses, pseudorabies viruses and retroviruses, and vectors derived from combinations of such viruses, such as those derived from plasmid and bacteriophage genetic elements, such as cosmids and phagemids. The expression system constructs may contain control regions that regulate as well as engender expression. Generally, any system or vector which is suitable to maintain, propagate or express polynucleotides and/or to express a polypeptide in a host can be used for expression. The appropriate DNA sequence can be inserted into the chosen expression by any of a variety of well-known and routine techniques, such as, for example, those set forth in Sambrook et al, *Molecular Cloning, A Laboratory Manual*, (supra).

Appropriate secretion signals, either homologous or heterologous, can be incorporated into the expressed polypeptide to allow the secretion of the protein into the lumen of the endoplasmic reticulum, the periplasmic space or the extracellular environment.

The polypeptides of the present invention can be recovered and purified from recombinant cell cultures by any of a number of well known methods, including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. It is most preferable to use high performance liquid chromatography (HPLC) for purification. Any of the well known techniques for protein refolding can be used to regenerate an active confirmation if the polypeptide is denatured during isolation and/or purification.

This invention is also related to the use of the polynucleotides of the invention as diagnostic reagents. Detection of a mutated form of a gene can be used as a diagnostic tool that to assist in the diagnosis of a disease or of susceptibility to a disease which results from under-expression, over-expression or altered expression of the gene. A variety of well known techniques can be used to detect, at the DNA level, an individual who has a mutation in the gene.

Nucleic acids for diagnosis may be obtained from an infected individual's cells and tissues, such as bone, blood, muscle, cartilage and skin. Genomic DNA can be used directly for detection or can be amplified prior to analysis using PCR or other amplification techniques. RNA or cDNA can also be used in the same manner. Deletions and insertions can be detected by a change in the size of the amplified product as compared to the genotype of a reference sequence. Point mutations can be identified by hybridizing amplified DNA to labeled polynucleotide sequences of the invention. Sequences that are perfectly matched can be distinguished from mismatched duplexes by RNase digestion or by differences in the melting temperature. Sequence differences can also be detected, at the DNA level, by comparing electrophoretic mobility of DNA fragments in gels, with or without denaturing agents; or by direct DNA sequencing (See, for example, Myers et al., *Science* 230: 1242 (1985)). A sequence change at a particular location can also be detected using nuclease protection assays, such as RNase and S1 protection or a chemical cleavage method (See, for example, Cotton et al., *Proc. Natl. Acad. Sci.*, USA, 85: 4397–4401 (1985). It is anticipated that an array of oligonucleotide probes comprising a DAGAT nucleotide sequence or fragments thereof can be used for screening, particularly for genetic mutations. Array technology methods are well known and are useful in gene expression, genetic linkage and genetic variability analyses (See, for example, M. Chee et al., *Science*, 274: 610–613 (1996)).

The invention further provides a method for diagnosing or determining a susceptibility to a disease associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders, obesity; diseases associated with abnormal lipid metabolism; diseases associated with abnormal fat absorption, lipoprotein secretion and adipogenesis, by determining from a sample an abnormally altered level of polypeptide or mRNA. Altered expression can be measured at the RNA level by any of the techniques well known in the art for quantitation of polynucleotides, including, but not limited to, amplification, PCR, RT-PCR, RNase protection, Northern blotting and other hybridization methods. Diagnostic assays are also contemplated which detect levels of protein expression including, but not limited to radioimmunoassays, competitive-binding assays, Western Blot analysis and ELISA assays.

The nucleotide sequences of the present invention can also be used in chromosome identification.

The polypeptides of the invention or variants thereof, or cells expressing them can be used as an immunogen to produce antibodies which are immunospecific for polypeptides of the present invention. "Immunospecific" means that the antibodies have a substantially greater affinity for the polypeptides of the present invention as compared to the affinity of the antibodies for other related polypeptides. "Antibodies" includes monoclonal and polyclonal antibodies, including chimeric, single chain, simianized, humanized, resurfaced and other types of complementarity determining region (CDR) replaced antibodies, as well as Fab fragments, including products of an Fab immunoglobulin expression library.

Antibodies can be obtained by administering the polypeptides or epitope bearing fragments, analogs or cells to an animal, preferably non-human, using routine protocols. Any of the well known techniques continuous cell culturing techniques can be used to prepare monoclonal antibodies including hybridoma technology (See for example, Kohler, G. and Milstein, C., *Nature* 256:495–497 (1975)); trioma technology; human B-cell hybridoma technology (Kozbor et al., *Immunology Today* 4:72 (1983)); and the EBV-hybridoma technology (Cole et al., *Monoclonal Antibodies and Cancer Therapy*, Alan R. Liss, 77–96, (1985)).

Single chain, humanized, resurfaced, simianized and other types of CDR replaced antibodies can be produced according to techniques which are well known in the art.

The described antibodies can be used to isolate or identify clones that express the polypeptide or to purify polypeptides by affinity chromatography. The antibodies can also be used to treat diseases associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The present invention also relates to genetically engineered soluble fusion proteins which comprises a polypeptide of the present invention, or a fragment thereof, fused to portions of the constant regions of the heavy or light chains of immunoglobulins of the various subclasses (IgG, IgM, IgA and IgE). Preferably the constant portion of the heavy chain of human IgG, particularly IgG1, is used with fusion at the hinge region. Particularly preferred is the use of Fc portion. (See, for example, WO 94/29458 and WO 94/22914).

Polypeptides of the present invention can also be used to identify compounds which bind to the polypeptide, and in particular, inhibit or stimulate the activity of the polypeptide by binding. The binding of small molecule substrates and ligands can be assessed in, for example, cells, cell-free preparations, chemical libraries, and natural product mixtures. The agonists or antagonists/inhibitors can be natural substrates or ligands or can be structural or functional mimetics thereof. See, for example, Coligan et al., Curr Prot in Immuno, 1(2):Chapter 5 (1991).

The invention also provides a method for screening compounds to identify those compounds that bind to the polypeptides or polynucleotides of the present invention and particularly those compounds that enhance (agonist) or inhibit (antagonist) the action of polypeptides or polynucleotides of the invention. High throughput screening techniques can be used. As an example, to screen for agonists or antagonists, a synthetic reaction mix, a cellular compartment, such as a membrane, cell envelope or cell wall, or a preparation of any of these, comprising a polypeptide of the invention and a labeled substrate or ligand of such polypeptide is incubated in the absence or presence of a candidate compound that is being screening. The ability of the candidate compound to agonize or antagonize a polypeptide of the invention is detected by a decrease in binding of the labeled ligand or a decrease in the production of product from the substrate. Candidate compounds that bind gratuitously, without inducing the effects of a polypeptide of the invention, are most likely to be good antagonists. On the other hand, compounds that bind well and increase the rate of product production from substrate are considered agonists. The detection of the rate or level of production of product from substrate can be enhanced by using a reporter system such as, but not limited to, colorimetric labeling, inclusion of a reporter gene that is responsive to changes in polynucleotide or polypeptide activity and binding assays known in the art.

Competitive assays that combine a polypeptide of the invention and a potential antagonist with a compound that binds the polypeptide, natural substrates or ligands, or substrate or ligand mimetics can also be used to screen for antagonist compounds. The polypeptide of the invention can be label, such as by radioactivity or colorimetric compound, such that the number of such polypeptide molecules that bound to the binding molecule or converted to product can be determined to assess the effectiveness of the potential antagonist.

Potential antagonists can include, but are not limited to, small organic molecules, peptides, polypeptides and antibodies that bind to a polynucleotide or polypeptide of the invention and thereby inhibit or partially or completely block its activity. Antagonists can also include small organic molecules, peptides, polypeptides and antibodies that bind to the same site on a binding molecule without inducing the activities that are induced by a polypeptide of the invention, thereby preventing the action of the polypeptide by blocking it from binding. Potential antagonists also include small molecules that bind to and occupy the binding site of the polypeptide thereby preventing the polypeptide from binding to cellular binding molecules, so as to prevent or reduce normal biological activity of the polypeptide. Examples of such small molecules include, but are not limited to, small organic molecules, peptides and peptide like molecules. Other potential antagonists include antisense molecules (see, for example, Okano, *J. Neurochem*, 56: 560 (1991); Oligodeoxynucleotides as Antisense Inhibitors of Gene Expression, CRC Press, Boca Raton, Fla. (1988)).

Antagonists and agonists of DAGAT activity are particular useful as DAGAT is important in the formation of chylomicra in small intestine, VLDL in liver, and for storage of energy as triacylglycerol in adipose tissue. Thus, inhibiting DAGAT activity in small intestine, liver, and adipose tissues will reduce lipid absorption and plasma triglyceride levels and will decrease adipogenesis. Further, hypertriglyceridemia has been shown to be an independent risk factor for atherosclerosis (Kugiyarna, K., et al., (1998) *Circulation* 97:2519–2526,) and is a marker for increased risk of coronary artery disease and can serve as a marker for several atherogenic factors. (Grundy, S. M., (1998) *Am. J. Cardiol*, 81:18B–25B). Compounds that inhibit DAGAT activity are also useful in controlling intestinal fat absorption, altering TAG rich lipoprotein secretion and controlling serum TAG, and reducing adipogenesis (Owen M R, et al. (1997) *Biochem J* 323:17–21, Jamdar S C and Cao W F (1995) *Biochim Biophys Acta* 1255:237–243). Furthermore, the diacylglycerol substrate of DAGAT is a signal transducing molecule within the cell and is a known modulator of protein kinase C activity. Altered cellular diacylglycerol concentration and PROTEIN KINASE C activity has been associated with cancer (da Costa et al.,(1993) *J. Biol. Chem.* 268:2100–2105), diabetes (Koya D and King G L (1998) *Diabetes* 47:859–866), heart failure (Okumura, et al., (1991) *J. Mol. Cell. Cardiol.* 23:409–416), adipocyte (Baldo et al., (1995) *J. Lipid Res.*, 36:1415–1426), leukemia and skin carcinoma cells (Goldkorn T., and Ding, T. (1997) *Adv. Exp. Med. Biol.*, 400A:461–472), and rat fibroblasts (Pai et al., (1991) *Proc. Natl. Acad. Sci.*, 88:598–602). As such, agonists and antagonists of the invention are particularly useful in treating or ameliorating diseases associated with DAGAT activity, including diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The invention also relates to compositions comprising the polynucleotide or the polypeptide, or variants, agonists or antagonists thereof. The polypeptides of the invention can be used in combination with a sterile or non-sterile carrier or carriers for use with cells, tissues or organisms, such as a pharmaceutical carrier suitable for administration to a subject. Such compositions comprise, for example, a therapeutically effective amount of a polypeptide or other compound of the invention and a pharmaceutically acceptable carrier or excipient. Such carriers include, but are not limited to, saline, buffered saline, dextrose, water, glycerol, ethanol and combinations thereof. The formulation should be consistent with the mode of administration. The invention further relates to diagnostic and pharmaceutical packs or kits comprising one or more containers filled with one or more of the ingredients of the aforementioned compositions of the invention.

Polypeptides and other compounds of the invention may be administered alone or in combination with other compounds.

The pharmaceutical compositions can be administered in any effective, convenient manner including, but not limited to, topical, oral, anal, vaginal, intravenous, intraperitoneal, intramuscular, subcutaneous, intranasal or intradermal routes.

The required dosage range will depend on the peptide or other compound of the present invention that is used, the route of administration, the nature of the formulation, the nature of the subject's condition and the judgment of the practitioner. Suitable dosages will generally be in the range of approximately 0.1 to 100 µg/kg. The large variation in the dosage is expected due to the variety of compounds and the differences in the efficacy of administration. As an example, it is expected that oral administration would require higher dosages than intravenous administration. The skilled practitioner can determine the appropriate dosage using standard empirical methods.

Polypeptides can also be generated endogenously in the subject, which is generally referred to as "gene therapy" For example, cells from a subject may be engineered with a polynucleotide, such as a DNA or RNA, to encode a polypeptide, ex vivo, and by the use of a retroviral plasmid vector. The cells are then introduced into the subject.

The polynucleotide and polypeptide sequences can also be used to identify additional sequences which are homologous to the sequences of the present invention. The most preferable and convenient method is to store the sequence in a computer readable medium, for example, floppy disk, CD ROM, hard disk drives, external disk drives and DVD, and then to use the stored sequence to search a sequence database with well known searching tools. Examples of public databases include the DNA Database of Japan (DDBJ) (www-ddbj.nig.ac.jp/) Genebank (www-ncbi.nlm.nih.gov/web/Genbank/Index.htlm); and the European Molecular Biology Laboratory Nucleic Acid Sequence Database (EMBL) (www-ebi.ac.uk/ebi_docs/embl_db.html). A number of different search algorithms are available to the skilled artisan, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology,* 12: 76–80 (1994); Birren, et al., *Genome Analysis,* 1: 543–559(1997)). Additional programs are available in the art for the analysis of identified sequences, such as sequence alignment programs, programs for the identification of more distantly related sequences, and the like, and are well known to the skilled artisan.

The invention now being generally described, it will be more readily understood by reference to the following examples which are included for purposes of illustration only and are not intended to limit the present invention.

EXAMPLES

Example 1

RNA Isolations

Total RNA from the inflorescence and developing seeds of *Arabidopsis thaliana* is isolated for use in construction of complementary (cDNA) libraries. The procedure is an adaptation of the DNA isolation protocol of Webb and Knapp (D. M. Webb and S. J. Knapp, (1990) Plant Molec. Reporter, 8, 180–185). The following description assumes the use of 1 g fresh weight of tissue. Frozen seed tissue is powdered by grinding under liquid nitrogen. The powder is added to 10 ml REC buffer (50 mM Tris-HCl, pH 9, 0.8M NaCl, 10 mM EDTA, 0.5% w/v CTAB (cetyltrimethyl-ammonium bromide)) along with 0.2 g insoluble polyvinylpolypyrrolidone, and ground at room temperature. The homogenate is centrifuged for 5 minutes at 12,000× g to pellet insoluble material. The resulting supernatant fraction is extracted with chloroform, and the top phase is recovered.

The RNA is then precipitated by addition of 1 volume RecP (50 mM Tris-HCL pH 9, 10 mM EDTA and 0.5% (w/v) CTAB) and collected by brief centrifugation as before. The RNA pellet is redissolved in 0.4 ml of 1M NaCl. The RNA pellet is redissolved in water and extracted with phenol/chloroform. Sufficient 3M potassium acetate (pH 5) is added to make the mixture 0.3M in acetate, followed by addition of two volumes of ethanol to precipitate the RNA. After washing with ethanol, this final RNA precipitate is dissolved in water and stored frozen.

Example 2

Identification of ACAT Sequences

Since plant ACATs are unknown in the art, searches are performed to identify known and related ACAT sequences from mammalian sources from public databases. These sequences are then used to search public and proprietary EST databases to identify plant ACAT-like sequences.

A public database containing mouse Expressed Sequence Tag (EST) sequences (dBEST) is searched for ACAT-like sequences. The search identified two sequences (SEQ ID NOs:12 and 13) which are related (approximately 20% identical), but divergent, to known ACAT sequences.

In order to identify ACAT-like sequences from other organisms, the two mouse ACAT sequences are used to search public and proprietary databases containing EST sequences from human and rat tissues. Results of the search identified approximately 180 sequences from the human database, which were assembled into a complete inferred cDNA sequence (FIG. 7) (SEQ ID NO:14) and approximately 35 from the rat database, also assembled into an inferred cDNA sequence using the GCG assembly program (FIG. 8) (SEQ ID NO:15) which are closely related to the mouse sequences.

Figure 9B:
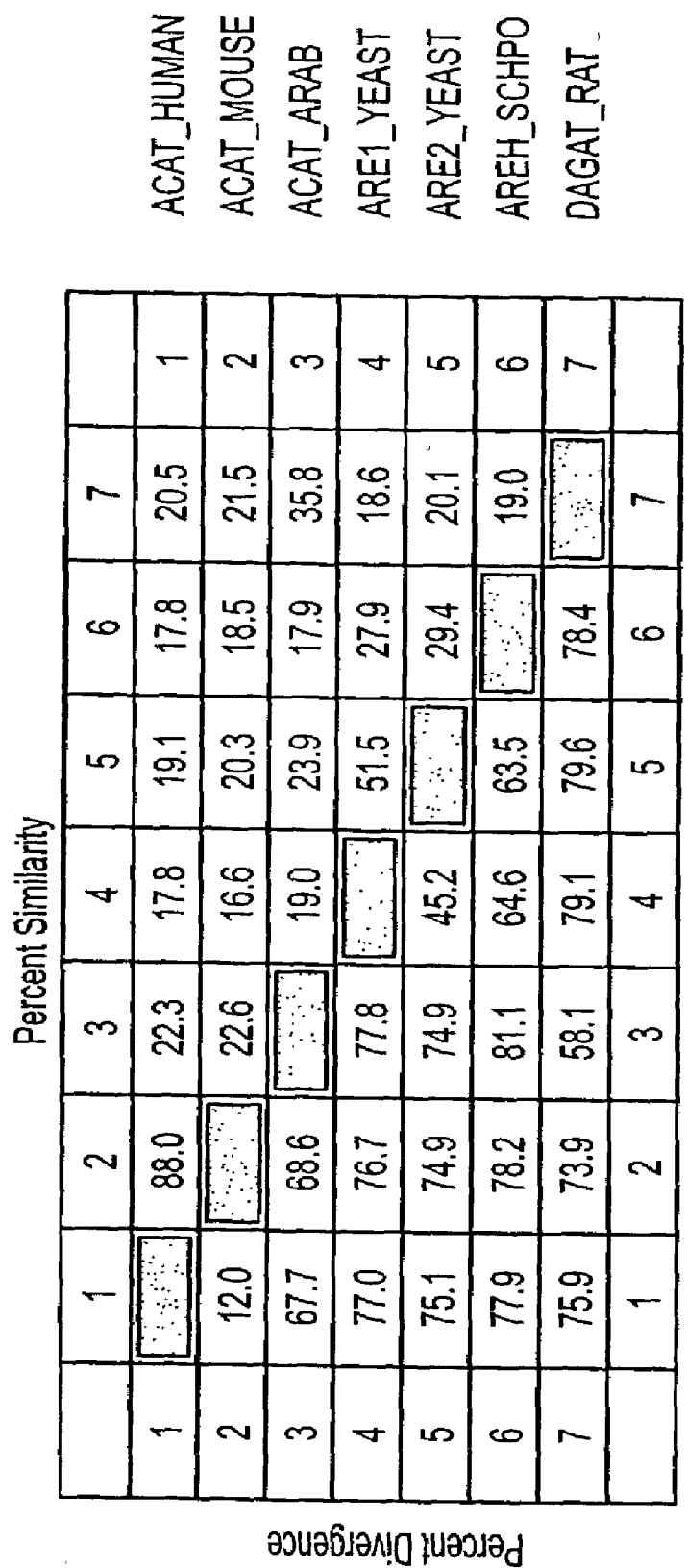
FIG. 9B provides a table showing the percent similarities and percent divergence of the known ACAT protein sequences and the novel ACAT-like sequences.

The protein sequence of the human ACAT-like sequence was aligned with known ACAT sequences from human (Chang, et al. (1993) *J. Biol. Chem.* 268:20747–20755, (SEQ ID NO:22)), mouse (Uelmen, et al. (1995) *J. Biol. Chem.* 270:26192–26201, (SEQ ID NO:23)) and yeast (Yu, et al. (1996) *J. Biol. Chem.* 271:24157–24163, (SEQ ID NO:24) and Yang, et al. (1996) *Science* 272:1353–1356, (SEQ ID NO:25)) using MacVector (Oxford Molecular, Inc.). Results of the alignment (FIG. 9) suggests that the sequence is related to the known sequences, however the related sequence is only about 25% similar to the known sequences.

The protein sequence of the human sterol O-acyltransferase (ACAT, Acyl CoA:Cholesterol acyltransferase, Accession number A48026)) (SEQ ID NO:15) related sequence was used to search protein and nucleic acid Genbank databases. A single plant homologue (FIG. 1) was identified in the public *Arabidopsis* EST database (Accession A042298, SEQ ID NO:1). The protein sequence was translated from the EST sequence, and was found to contain a peptide sequence conserved in both mammalian and yeast ACATs (Chang et al., (1997) *Ann. Rev. Biochem.,* 66:613–638)) (SEQ ID NO:21).

To obtain the entire coding region corresponding to the *Arabidopsis* ACAT-like EST, synthetic oligo-nucleotide primers are designed to amplify the 5' and 3' ends of partial cDNA clones containing ACAT-like sequences. Primers are designed according to the *Arabidopsis* ACAT-like EST sequence and are used in Rapid Amplification of cDNA Ends (RACE) reactions (Frohman et al. (1988) *Proc. Natl. Acad. Sci. USA* 85:8998–9002).

Primers are designed (5'-TGCAAATTGACGAGCA-CACCAACCCCTTC-3' (SEQ ID NO:26) and 5'-AAGGAT-GCTTTGAGTTCCTGACAATAGG-3' (SEQ ID NO:27) to amplify the 5' end from the *Arabidopsis* ACAT EST sequence. Amplification of flanking sequences from cDNA clones are performed using the Marathon cDNA Amplification kit (Clontech, CA).

Sequence derived from the 5'-RACE amplification is used to search proprietary *Arabidopsis* EST libraries. A single EST accession, LIB25-088-C7 (SEQ ID NO:1), is identified which contains sequence identical to the 5'-RACE sequence. Furthermore, LIB25-088-C7 is found to contain the complete putative coding sequence for the *Arabidopsis* ACAT-like product ) (SEQ ID NO:1).

The nucleic acid as well as the putative translation product sequences of A042298 were used to search public and proprietary databases. Four EST sequences are identified in both soybean (FIG. 2) (SEQ ID NO:3–6) and maize (FIG. 3) (SEQ ID NO:7–10) proprietary databases, and a single ACAT-like sequence is identified from *Mortierrella alpina* EST sequences (FIG. 4) (SEQ ID NO:11).

The rat ACAT-like DNA sequence derived from the assembly of single pass 5' terminal sequences of a number of cDNA sequences (SEQ ID NO:15) does not contain a single open reading frame, due to errors in the sequence obtained. Thus, the DNA sequence coding for the full length Rat ACAT-like sequence is obtained using RACE reactions for use in expression construct preparation.

A rat cDNA clone (# 700938833)) (SEQ ID NO:15), which is homologous to the rat ACAT-like sequence described above (FIG. 8) is obtained, and its DNA sequence is determined. The largest open reading frame extended to the 5' end of the clone, suggesting that the cDNA is not long enough to encode the entire protein.

A cDNA clone representing the 5'end of the ACAT-like gene is isolated using RAT Marathon-Ready cDNA derived from rat adipocyte tissue (Clontech #7481-1) according to the manufacturer's protocol. The primary PCR reaction is carried out using the gene specific primer 5'-TAGGTGA-CAGACTCAG CATTCCACCAGTCCC-3' (SEQ ID NO:28), and a nested PCR reaction is carried out using the gene specific primer 5'-CGCCAGCTTTAAGAGACGCT-CAAT GATTCG-3' (SEQ ID NO:29). The nested PCR yields a prominent product approximately 900 nucleotides in length. The PCR product is cloned into plasmid pCR2.1 according to the manufacturer's protocol (Invitrogen). The sequence of several clones was determined. Although the open reading frame extends to the 5' end of the cDNA, the prominent PCR product of a discrete size in the 5'RACE reaction suggests that the 5' end of the clone represents the 5' end of the mRNA. It remains a possibility that the protein is larger than the protein inferred from the DNA sequence of the presently described cDNA. The sequence of the 5'RACE products and the clone were assembled to yield the sequence described in this application (FIG. 10) (SEQ ID NO:16).

The primers 5'-GGATCCCTGCAGGTCAGGC-CCCCACTGGGGCATCATA-3' (SEQ ID NO:30) and 5'-GGATCCGCGGCCGCACAATGGGCGAC-CGCGGAGGCGCGGGA-3' (SEQ ID NO:31) are used to PCR amplify the open reading frame (ORF) from rat adipocyte Marathon Ready cDNA (clontech). These primers introduce NotI and Sse83871 restriction sites at the 5' and 3' ends of the ORF, respectively. The PCR product was cloned into plasmid pCR2.1 according to the manufacturer's protocol (Invitrogen) to yield plasmid pCGN8592. The complete nucleotide sequence and deduced amino acid sequence for the rat ACAT-like gene are shown in FIGS. 10 (SEQ ID NO:16) and 11 (SEQ ID NO:17), respectively. For expression of the Rat ACAT-like protein in insect cells using a baculovirus expression system, the NotI-Sse83871 fragment of pCGN8592 was cloned into NotI-PstI digested plasmid pFASTBAC1 (Gibco), and the resultant plasmid pCGN9704, was transformed into *E. coli* DH10BAC (Gibco) to generate bacmid9704. The bacmid DNA was used to transfect insect cells.

The rat ACAT-like protein sequence was used to query the Worm Pep database (www-sanger.ac.uk/Projects/C_el-egans/blast_server.shtml) using BlastP. One sequence, H19N07.4 (SEQ ID NO: 18), showed significant homology to the rat sequence. The nematode sequence was aligned to the rat ACAT-like sequence using the Clustal W alignment tool of Macvector (Oxford Molecular). After alignment, 45% of the amino acids are identical and 62% are similar or identical. The nematode protein is likely to harbor DAGAT activity and could be used to produce triglycerides in transgenic cells. *C. elegans* clone yk453a2 (SEQ ID NO: 19 and 20) appears to be a full length cDNA clone encoding the *C. elegans* protein (SEQ ID NO: 18). Both the 5, and 3' end sequences of this clone are present in Genbank. This sequence can be used to design PCR primer to amplify the ORF with suitable restriction sites for expression of the *C. elegans* protein in heterologous systems such as insect cells, plant cells, *E. coli* and other microbes. For example, the primers 5'-GGATCCGCGGCCGCACAATGCGTCAA-CAAACGGGACGACGG (SEQ ID NO: 32) and 5'-GGATCCCCTGCAGGTCAAATACCAACG-GTTTGGTTTTG (SEQ ID NO: 33) could be used to amplify the cDNA encoding the *C. elegans* protein. These primers introduce NotI and Sse83781 sites suitable for cloning the ORF for expression in plant, insect cell, and *E. coli* cells using vectors described elsewhere in this application.

Example 3

Sequence Comparisons

Sequence alignments between ACAT sequences from several different sources are compared to identify the similarity between the sequences. Nucleotide sequences from known human and mouse ACATs, as well as nucleotide sequences from known yeast ACATs are compared to the ACAT-like EST sequences from human and *Arabidopsis*.

Analysis of the sequence alignments reveals several classes of ACATs based on sequence similarity. The known human and mouse ACATs, being 88% similar in the nucleotide sequence, form one class of ACATs. Another class of ACATs includes the yeast ACATs which are less than 20% similar to the known human and mouse class ACATs.

The final class of ACATs includes the *Arabidopsis* (FIG. 1)) (SEQ ID NO:1) and human (FIG. 7)) (SEQ ID NO:14) sequences disclosed in the present invention. This class is approximately 22% similar to the known human and mouse ACAT class and approximately 23% similar to the yeast class of ACATs. Thus, the ACAT sequences disclosed in the present invention represent a novel class of ACAT enzymes. Partial mouse sequences of this class are also provided (FIGS. 5 and 6).

The cDNA obtained coding for the entire rat ACAT-like protein is 1766 nucleotides in length (FIG. 10). The protein coded by the DNA sequence is 500 amino acids in length (FIG. 11), and its molecular weight is 57 kDa. The reading frame is open upstream (5') of the methionine to the 5' terminus of the cDNA, thus it is possible that the protein is larger than that predicted by the cDNA sequence. When the rat ACAT-like protein sequence is aligned with the amino acid sequences of the human and mouse sequences, it is found that the rat sequence is 20% identical, and 34% similar. However, when the rat sequence is compared to the *Arabidopsis* ACAT-like protein sequence, the rat sequence is 30% identical and 44% similar.

Furthermore, sequence comparisons between the rat and *Arabidopsis* ACAT-like amino acid sequences and the known human and mouse ACAT sequences shows a peptide sequence, GAAAQNTVSYP (SEQ ID NO: 47), unique to the rat ACAT-like protein.

Example 4

Expression Constructs

4A. Baculovirus Expression Constructs

Constructs are prepared to direct the expression of the *Arabidopsis* ACAT-like sequence in cultured insect cells. The entire coding region of the *Arabidopsis* ACAT-like sequence is amplified from the EST clone LIB25-088-C7 using oligonucleotide primers 5'-TCGACCTGCAG-GAAGCTTAGAAATGGCGATTTTGGATTC-3') (SEQ ID NO:34)and 5'-GGATCCGCGGCCGCTCATGACATC-GATCCTTTTCGG-3') (SEQ ID NO:35) in a polymerase chain reaction (PCR). The PCR product was subcloned into pCR2.1 (Invitrogen). Double stranded DNA sequence was obtained to verify that no errors were introduced by PCR amplification. The resulting plasmid was designated pCGN8626.

pCGN8626 was digested with NotI and the 5' overhang was filled in with Klenow fragment. The plasmid was further digested with Sse8387I and a fragment containing the ACAT homologue coding region was purified by gel electrophoresis. The fragment containing the entire coding region of the *Arabidopsis* ACAT-like sequence was subcloned into baculovirus expression vector pFastBac 1 (Gibco-BRL, Gaithersburg, Md.) that had been digested with HindIII, blunt-ended by filling in the 5' overhand with Klenow fragment and then digesting with PstI. The resulting plasmid was designated pCGN8631. DNA sequence analysis confirmed the integrity of the cloning junctions.

4B. Plant Expression Construct Preparation

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAA (SEQ ID NO:36) AT was ligated into the cloning vector pBC SK+ (Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGCT-TCCTGCAGG-3') (SEQ ID NO:37) and 5'-TCGACCTG-CAGGAAGCTTGCGGCCGCGGATCC-3') (SEQ ID NO:38) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGC-CGCGGATCC-3') (SEQ ID NO:39) and 5'-TCGAGGATC-CGCGGCCGCAAGCTTCCTGCAGG-3') (SEQ ID NO:40) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCT-TCCTGCAGGAGCT-3') (SEQ ID NO:41) and 5'-CCTG-CAGGAAGCTTGCGGCCGCGGATCC-3') (SEQ ID NO:42) into SalI/SacI-digested pCGN7787. A fragment containing the d35S promoter, polylinker and tml 3' region was removed from pCGN8620 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGC-CGCGGATCCAGCT-3') (SEQ ID NO:43) and 5'-GGATC-CGCGGCCGCAAGCTTCCTGCAGG-3') (SEQ ID NO:44) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

A fragment containing the *Arabidopsis* ACAT-like coding region was removed from pCGN8626 by digestion with Sse8387I and Not I. The fragment containing the ACAT-like sequence was ligated into PstI-Not I digested pCGN8622. The resulting plasmid was designated pCGN8627. DNA sequence analysis confirmed the integrity of the cloning junctions.

A fragment containing the *Arabidopsis* ACAT-like coding region was removed from pCGN8626 by digestion with Sse8387I and Not I. The fragment was ligated into PstI-Not I digested pCGN8623. The resulting plasmid was designated pCGN8628. DNA sequence analysis confirmed the integrity of the cloning junctions.

A fragment containing the *Arabidopsis* ACAT-like coding region was removed from pCGN8626 by digestion with Sse8387 and Not I. The fragment was ligated into PstI-Not I digested pCGN8624. The resulting plasmid was designated pCGN8629. DNA sequence analysis confirmed the integrity of the cloning junctions.

A fragment containing the *Arabidopsis* ACAT-like coding region was removed from pCGN8626 by digestion with Sse8387 and Not I. The fragment was ligated into PstI-Not I digested pCGN8625. The resulting plasmid was designated pCGN8630. DNA sequence analysis confirmed the integrity of the cloning junctions.

An additional expression construct for the suppression of endogenous ACAT-like activity was also prepared. The construct pCGN8660 was constructed by cloning approximately 1 Kb of the *Arabidopsis* ACAT-like coding region from pCGN8626 in the sense orientation, and the full-length *Arabidopsis* ACAT-like coding region in the antisense orientation under the regulatory control of the napin transcription initiation sequence.

For expression of the rat ACAT-like sequence in plants, the NotI-Sse8387I fragment of pCGN8592 was cloned into NotI-PstI digested binary vectors pCGN8621, pCGN8622, and pCGN8624 to yield plasmids, pCGN 9700, pCGN9701, and pCGN9702, respectively. Plasmid pCGN9700 expresses a sense transcript of the rat ACAT-like cDNA under control of a napin promoter, plasmid pCGN9701 expresses an antisense transcript of the rat ACAT-like cDNA under control of a napin promoter, and plasmid pCGN9702 expresses a sense transcript of the rat ACAT-like cDNA under control of a double 35S promoter. Plasmids pCGN 9700, pCGN970 1, and pCGN9702 are introduced in *Agrobacterium tumefaciens* EHA101.

Figure 15:
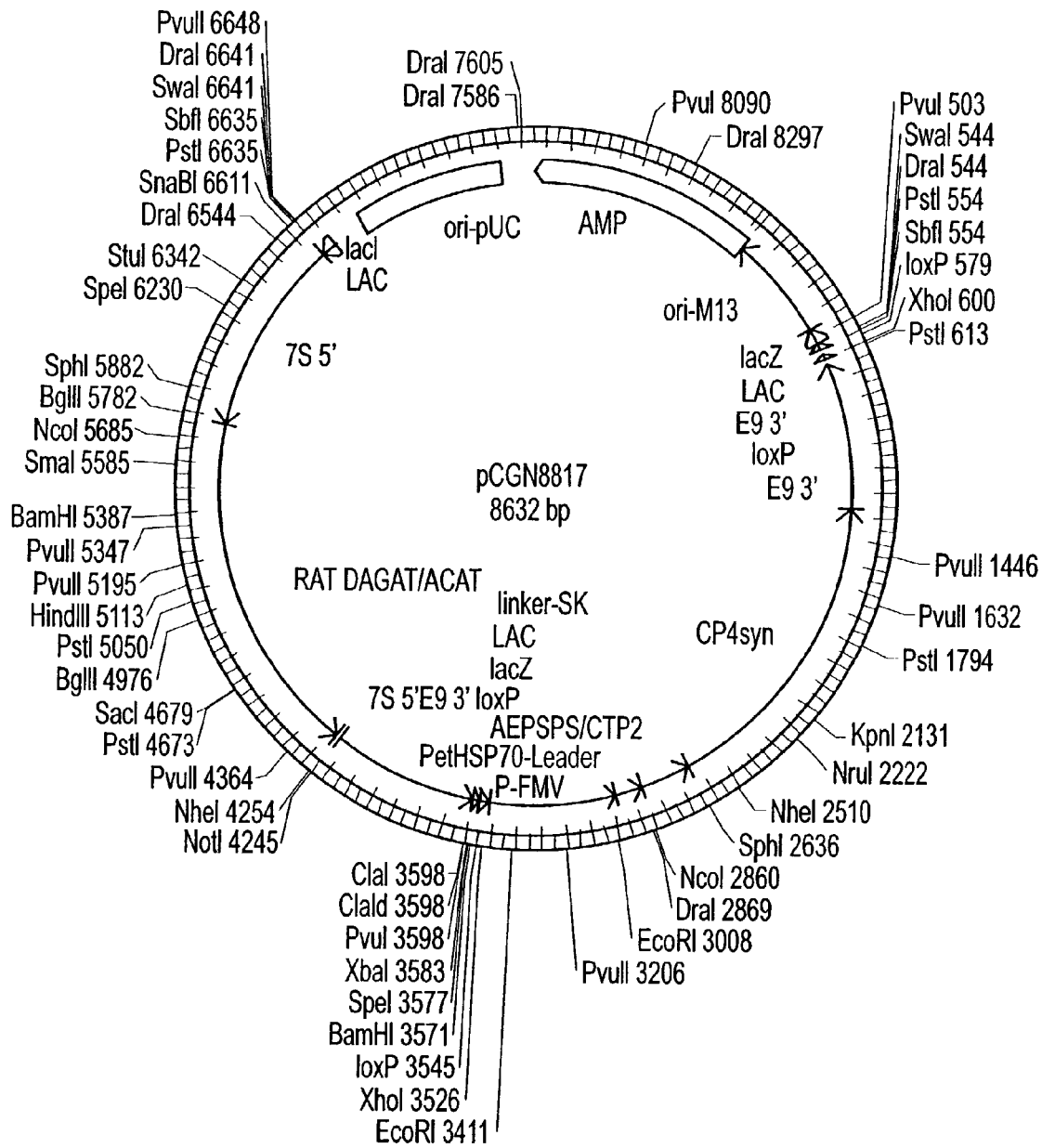
FIG. 15 provides a schematic diagram of the binary vector for soybean transformation, pCGN8817.

Constructs are prepared to direct the expression of the rat ACAT-like sequence in the seed embryo of soybean and the endosperm of corn. For expression of the rat ACAT-like DNA sequence in soybean, a 1.5 kb NotI/Sse8387I fragment from pCGN8592 containing the coding sequence of the rat ACAT-like sequence was blunt ended using Mung bean nuclease, and ligated into the SmaI site of the turbo 7S binary/cloning vector pCGN8809 to create the vector pCGN8817 (FIG. 15) for transformation into soybean by particle bombardment. The vector pCGN8817 contains the operably linked components of the promoter region of the soybean α' subunit of β-conglycinin (7S promoter, (Chen et al., (1986), *Proc. Natl. Acad. Sci.*, 83:8560–8564), the DNA sequence coding for the entire rat ACAT-like protein, and the transcriptional termination region of pea RuBisCo small subunit, referred to as E9 3' (Coruzzi, et al. (1984) *EMBO J.* 3:1671–1679 and Morelli, et al. (1985) *Nature* 315:200–204). This construct further contains sequences for the selection of positive transformed plants by screening for resistance to glyphosate using the CP4 EPSPS (U.S. Pat. No. 5,633,435) expressed under the control of the figwort mosaic virus (FMV) promoter (U.S. Pat. No. 5,378,619) and the transcriptional termination region of E9.

Figure 16:
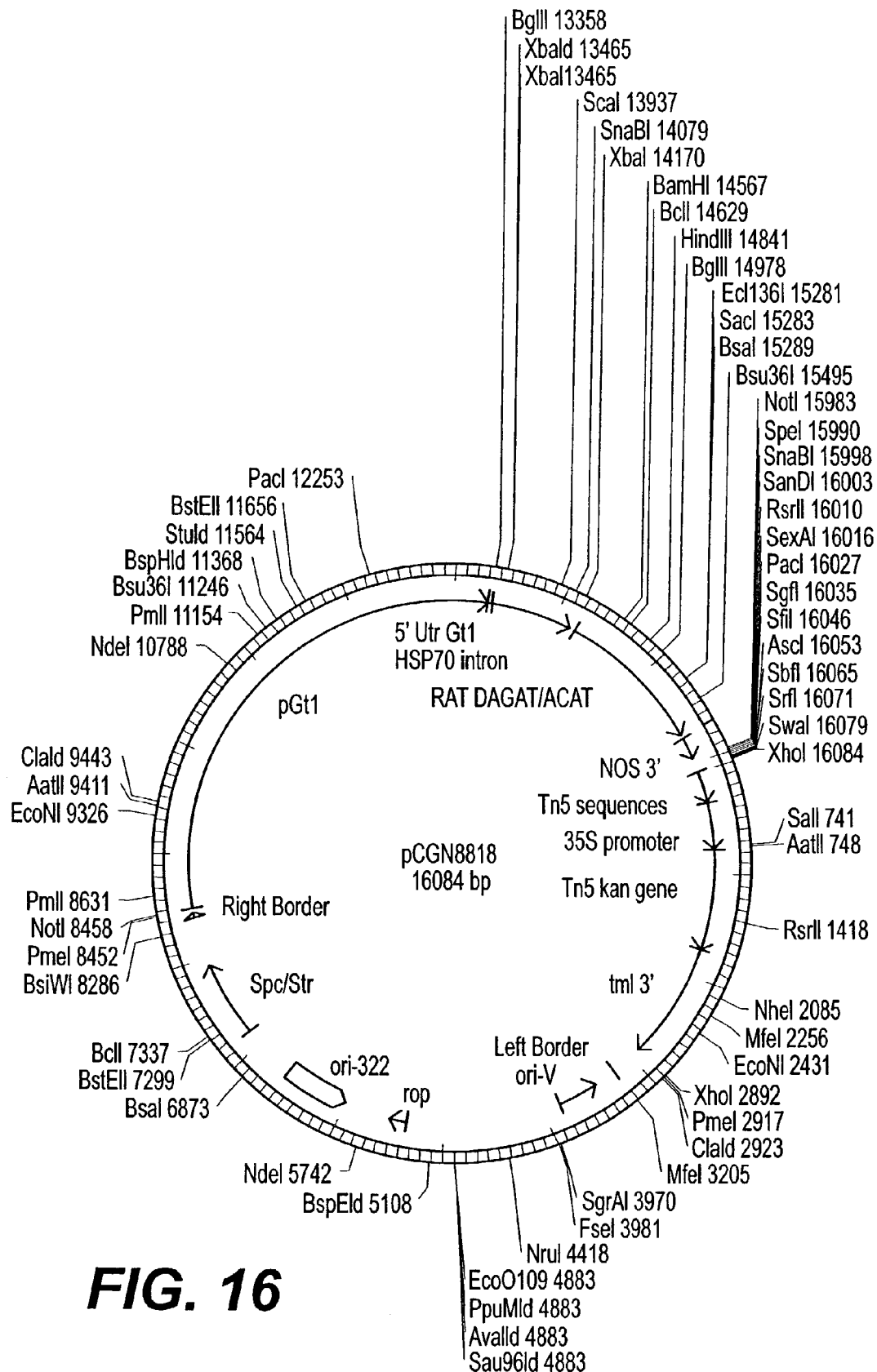
FIG. 16 provides a schematic diagram of the binary vector for transformation of corn, pCGN8818.

For expression of the rat ACAT-like sequence in the corn endosperm, a 1.5 kb NotI/Sse8387I fragment from pCGN8592 containing the coding sequence of the rat ACAT-like sequence was blunt ended using Mung bean nuclease, and ligated into the BamHI site of the rice pGt1 expression cassette pCGN8592 for expression from the pGt1 promoter (Leisy, D. J. et al., Plant Mol. Biol. 14 (1989) 41–50) and the HSP70 intron sequence (U.S. Pat. No. 5,593,874). This cassette also includes the transcriptional termination region downstream of the cloning site of nopaline synthase, nos 3' (Depicker et al., *J. Molec. Appl. Genet.* (1982) 1: 562–573). A 7.5 kb fragment containing the pGt1 promoter, the DNA sequence encoding the rat ACAT-like protein, and the nos transcriptional termination sequence is cloned into the binary vector pCGN8816 to create the vector pCGN8818 (FIG. 16) for transformation into corn. This construct also contains sequences for the selection of positive transformants with kanamycin using the kanamycin resistance gene from Tn5 bacteria under the control of the CAMV 35S promoter and tml transcriptional termination regions.

Example 5

Expression of ACATs in Insect Cell Culture

A baculovirus expression system is used to express the full length rat and *Arabidopsis* ACAT-like cDNA in cultured insect cells.

The baculovirus expression construct pCGN8631 is transformed and expressed using the BAC-to-BAC Baculovirus Expression System (Gibco-BRL, Gaithersburg, Md.) according to the maufacturers directions, except harvesting of recombinant viruses was done 5 days post-transfection. The supernatant from the transfection mixture is used for generating virus stock which in turn is used for infecting Sf9 cells for use in the assay.

The transformed insect cells may be assayed for ACAT, DAGAT or other acyltransferase activities using methods described herein. Insect cells are centrifuged and the resulting pelletted cells were resuspended in Medium 1 (0.25 M sucrose and 1 mM EDTA in 10 mM Tris-Cl, pH 7.4) and homogenized on ice. The homogenate is centrifuged at 105,000× g for 1 at 4° C. Total membranes are resuspended in Medium I. DAGAT activity is assayed in a 0.2 ml reaction mixture containing 175 mM Tris, pH 8, 1 mg/ml bovine serum albumin, 8 mM MgCl2, 0.2 mM 1,2-diolein in acetone, 20 mM 3H-palmitoyl-CoA, and 0.5–30 mg of membrane proteins. The final concentration of acetone is 10%. In some assays, to measure DAGAT activity under optimal conditions for plant enzyme, the 0.2 ml reaction mixture contained 0.1 M NaCl, 0.1% Triton X 100, 0.5 mM 1,2-diolein, 10 mM EDTA, 0.1 M Tris, pH 7.8, and 20 mM 3H-palmitoyl-CoA. The 10 min reaction is terminated by addition of 1.5 ml solution of isopropanol:heptane:water (80:20:2, v/v). The lipids are extracted and analyzed by thin layer chromatography as described (Coleman R. A. (1992) *Methods. Enzymol.* 209, 98–104).

The results of the DAGAT activity assay demonstrates that the RAT ACAT related DNA sequence encodes a protein with DAGAT activity about 80 fold greater than the controls.

Example 6

E. coli Expression of the Rat DAGAT

An *E. coli* expression vector was constructed by annealing the oligonucleotide primers 5'-CAGGAGGCGGCCG-CAGGAGGCTGCAGGTAC) (SEQ ID NO:45) and 5'-CCTGCAGCCTCCTGCGGCCGCCTCCTGAGCT) (SEQ ID NO:46) to make a synthetic adapter. The adapter was ligated to plasmid pBC SK+ (Stratagene) after digesting the plasmid with the restriction endonucleases, SstI and KpnI. The resultant plasmid was named pCGN9909. Plasmid pCGN9909 was digested with NotI and PstI and ligated with the NotI-Sse83871 fragment from pCGN8592. The resultant plasmid, containing the rat DAGAT ORF under control of the *E. coli* Lac promoter, was designated pCGN9720. Five ml cultures *E. coli* cultures of pCGN9909 and pCGN9720 were grown overnight at 30 degrees centigrade to stationary stage in ECLB+100 ug/ml ampicillin. The 5 ml cultures were added to 50 ml of ECLB+0.1 mM IPTG and 100 ug/ml ampicillin, and the cultures were grown for 4 hours at 30 degrees. The cells were pelleted, resuspended in 2 ml isopropanol, and incubated at 75 degrees centigrade for 30 minutes. The solution was cooled to room temperature and 3 ml of hexane were added. The cells were incubated with shaking for 1 hour, 3 ml of 6.6% sodium sulfite was added, the solution was vortexed, and the upper organic phase was removed to a clean test tube. The solvent was evaporated under a stream of nitrogen gas, and the lipids were resolved by TLC on silica G. The TLC plate was developed in hexane:diethyl ether:acetic acid (75:25:1). The lipids were visualized by staining with iodine. Triglycerides were observed in the *E. coli* transformed with pCGN9720, but not in the *E. coli* transformed with the empty vector pCGN9909 (FIG. 18). This suggests that the rat DAGAT can be used to produce triglycerides in microbes and other cells which otherwise would produce little or not triglyceride.

Example 7

Plant Transformation

A variety of methods have been developed to insert a DNA sequence of interest into the genome of a plant host to obtain the transcription or transcription and translation of the sequence to effect phenotypic changes.

The plant binary constructs pCGN8627, pCGN8628, pCGN8629 and pCGN8630 are used in plant transformation to direct the expression of the *Arabidopsis* ACAT-like sequence from plant tissues.

Transgenic *Brassica* plants are obtained by *Agrobacterium*-mediated transformation as described by Radke et al. (*Theor. Appl. Genet.* (1988) 75:685–694; *Plant Cell Reports* (1992) 11:499–505). Transgenic *Arabidopsis thaliana* plants may be obtained by *Agrobacterium*-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C.R.Acad.Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain nuclear transformed plants.

Example 8

Analysis of Transgenic Plants

Transgenic plants expressing proteins derived from the novel ACAT-like sequences are analyzed using techniques known in the art for sterol esterification activity and/or TAG synthesis activity. Enzyme assays are used to determine the enzyme activity of the ACAT-like translational product in plants transformed with pCGN8629, and plants transformed with pCGN8630. Leaf extracts are analyzed by thin layer chromatography to determine glycerolipid composition of the leaf lipids as well as sterol content. Seed extracts of the control plants, plants transformed with pCGN8627, and plants transformed with pCGN8628 are analyzed for alterations in the levels of diacylglycerol, triacylglycerol, or phospholipids as well as modifications of the sterol levels.

A single leaf was removed from each of 10–20 *Arabidopsis* plants. The leaves were weighed, and leaf lipids were extracted in 4 ml hexane:isopropanol (3:2). 2 ml of 6.6% sodium sulfite was added, the solution was vortexed, and the upper organic phase was removed to a fresh test tube. The solvent was dried under nitrogen gas, and the leaf neutral lipids were resuspended in 50 ul of hexane. The leaf lipids were resolved by TLC on Silica G TLC plates developed in hexane:diethyl ether:acetic acid (75:25: 1). After development, the lipids were visualized by staining with primulin (0.01% in 80% acetone) and viewing under long wave (350 nM) UV illumination. The lipids that migrated the same distance as a triglyceride standard were transmethylated in acidic methanol (8.5% H2SO4 in methanol for 2 hours) with 62.5 ug of a tri-17:0 triglyceride standard, and the fatty acid methyl esters (FAMES)were resolve by gas chromatography. The quantity of triglycerides was determined by comparing the peak area of the leaf triglyceride FAMEs with the area of the 17:0 internal standard. Leaves from untransformed control plants contained 0.041 ug TAG/mg fresh weight, while the leaves from pCGN9702 plants contained 0.49 ug TAG/mg fresh weight. Thus, expression of the rat ACAT-like cDNA in transgenic leaf tissue directed more than a 10 fold increase in the quantity of TAG in leaf tissue.

The above results demonstrate that the ACAT-like nucleic acid sequences identified in the present invention encode for proteins active in the formation triacylglycerol. Such nucleic acid sequences may be used in constructs to provide for the expression of the ACAT-like protein in host cells. Furthermore, such expression constructs may be employed in methods for modifying triacylglycerol content of host cells and organisms.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method of modifying the lipid composition in a plant cell, said method comprising:
   transforming a plant cell with a recombinant DNA construct comprising a DNA sequence of SEQ ID NO 16;
   growing said cell under conditions wherein transcription of said DNA sequence is initiated,
   whereby said lipid composition is modified.

2. The method according to claim 1, whereby the synthesis of triglycerides is increased in said plant cell.

3. The method according to claim 1, wherein said plant cell is selected from the group consisting of *Brassica*, corn, soybean, safflower, alfalfa, and sunflower.

4. A method of modifying the lipid composition in a plant cell, said method comprising:
   transforming a plant cell with a recombinant DNA construct that encodes a protein comprising an amino acid sequence of SEQ ID NO: 17;
   growing said cell under conditions wherein said protein is expressed,
   whereby said lipid composition is modified.

5. The method according to claim 4, whereby the synthesis of triglycerides is increased in said plant cell.

6. The method according to claim 4, wherein said plant cell is selected from the group consisting of *Brassica*, corn, soybean, safflower, alfalfa, and sunflower.

7. An isolated nucleic acid molecule comprising the sequence of SEQ ID NO: 16.

8. An isolated nucleic acid molecule comprising a nucleotide sequence that encodes a polypeptide comprising SEQ ID NO: 17.

9. A recombinant nucleic acid construct comprising a nucleic acid sequence of SEQ ID NO: 16.

10. A recombinant nucleic acid construct comprising a nucleic acid sequence that encodes a protein comprising an amino acid sequence of SEQ ID NO: 17.

11. The method according to claim 1, whereby the quantity of triglycerides is increased by more than 10 fold in said plant cell.

12. The method according to claim 4, whereby the quantity of triglycerides is increased by more than 10 fold in said plant cell.

13. The recombinant nucleic acid construct of claim 9, comprising a promoter functional in plant cells operably linked to a nucleic acid sequence of SEQ ID NO: 16 in antisense orientation.

14. The recombinant nucleic acid construct of claim 10, comprising a promoter functional in plant cells operably linked to a nucleic acid sequence that encodes a protein comprising the amino acid sequence of SEQ ID NO: 17, wherein said nucleic acid sequence that encodes a protein comprising an amino acid sequence of SEQ ID NO: 17 is in antisense orientation.

* * * * *